(12) United States Patent
Kiyuna et al.

(10) Patent No.: US 9,230,154 B2
(45) Date of Patent: Jan. 5, 2016

(54) INFORMATION PROCESSING APPARATUS, METHOD, AND STORAGE MEDIUM FOR ASSISTING WITH A DIAGNOSIS BASED ON A TISSUE SAMPLE

(75) Inventors: Tomoharu Kiyuna, Tokyo (JP); Tomofumi Hiratsuka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 125 days.

(21) Appl. No.: 13/981,275

(22) PCT Filed: Jan. 10, 2012

(86) PCT No.: PCT/JP2012/050249
§ 371 (c)(1),
(2), (4) Date: Jul. 23, 2013

(87) PCT Pub. No.: WO2012/102069
PCT Pub. Date: Aug. 2, 2012

(65) Prior Publication Data
US 2013/0301900 A1    Nov. 14, 2013

(30) Foreign Application Priority Data

Jan. 24, 2011    (JP) .................................. 2011-012425

(51) Int. Cl.
*G06K 9/00* (2006.01)
*G06F 19/00* (2011.01)
*G06K 9/62* (2006.01)

(52) U.S. Cl.
CPC .......... *G06K 9/00147* (2013.01); *G06F 19/321* (2013.01); *G06F 19/3418* (2013.01); *G06K 9/00127* (2013.01); *G06K 9/6253* (2013.01)

(58) Field of Classification Search
None
See application file for complete search history.

(56) References Cited

U.S. PATENT DOCUMENTS

2006/0241979 A1    10/2006    Sato et al.
2012/0082366 A1    4/2012    Marugame

FOREIGN PATENT DOCUMENTS

| JP | 2000-287955 A | 10/2000 |
|---|---|---|
| JP | 2001-005950 A | 1/2001 |
| JP | 2004-500211 A | 1/2004 |
| JP | 2006-153742 A | 6/2006 |
| JP | 2006-326287 A | 12/2006 |
| JP | 2010-097482 A | 4/2010 |
| WO | 01/75776 A1 | 10/2001 |
| WO | 2010/140588 A1 | 12/2010 |

*Primary Examiner* — Atiba O Fitzpatrick
(74) *Attorney, Agent, or Firm* — Sughrue Mion, PLLC

(57) ABSTRACT

This invention relates to an information processing apparatus which assists diagnosis based on a tissue sample image obtained by staining and capturing a tissue. The information processing apparatus receives and analyzes lower magnification image data among a plurality of image data obtained at different magnifications for an area image selected in the tissue sample image. Based on the analysis result, the information processing apparatus determines whether analysis based on higher magnification image data is necessary. When analysis based on the higher magnification image data is necessary, the information processing apparatus notifies a request of transmitting the higher magnification image data for the area image, receives and analyzes the higher magnification image data transmitted in response to the transmission request, and transmits the analysis result. This arrangement can quickly provide high-accuracy diagnosis assistance for a tissue sample image from a pathologist regardless of the restriction of the transmission capacity.

14 Claims, 26 Drawing Sheets

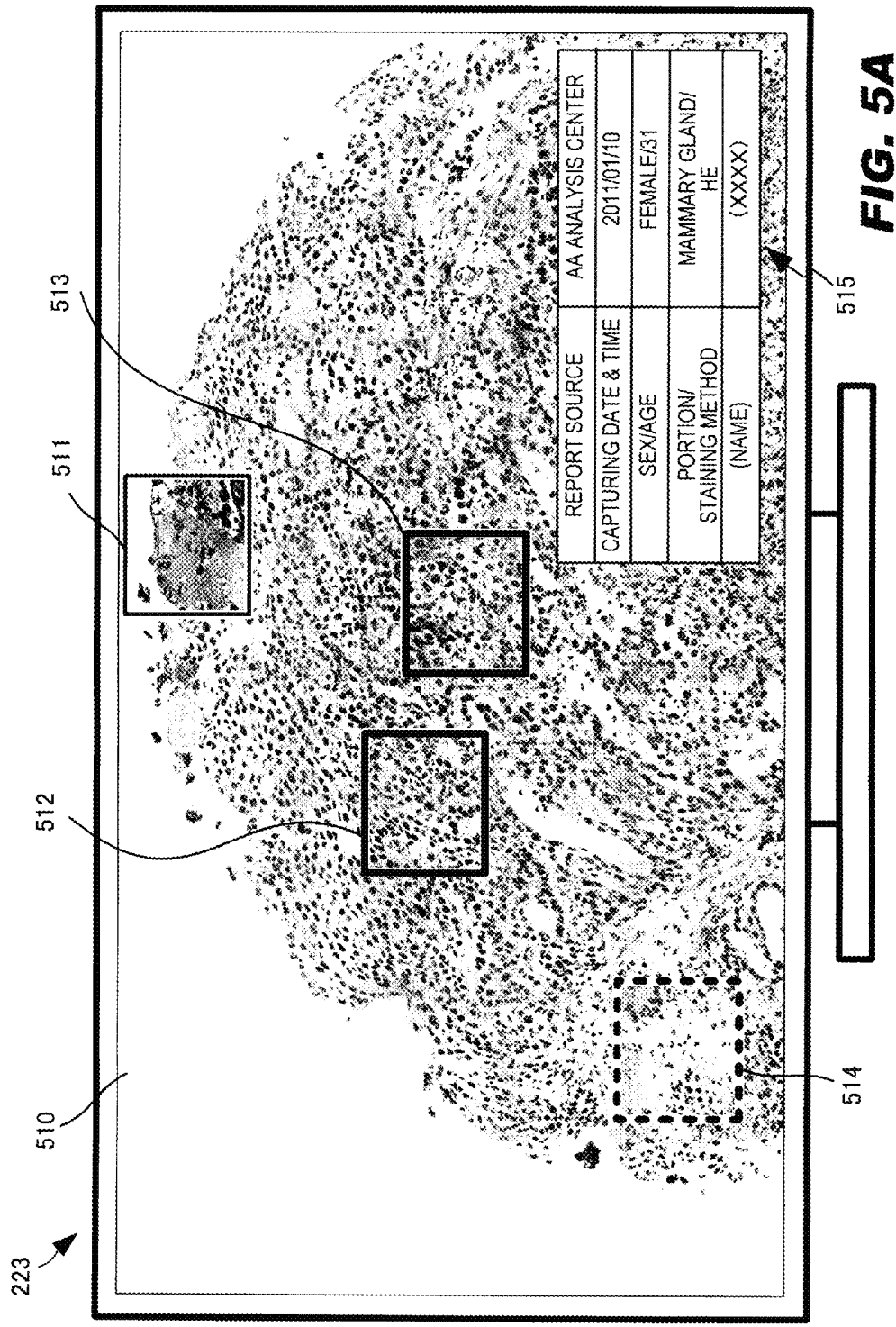

| TERMINAL ID 701 | RECEIVED IMAGE NUMBER 702 | LOW-MAGNIFICATION IMAGE DATA 703 | PORTION 704 | STAINING METHOD 705 | SEX/AGE 706 | TISSUE STRUCTURE ANALYSIS RESULT 707 | NECESSITY OF HIGH-MAGNIFICATION IMAGE 708 |
|---|---|---|---|---|---|---|---|
| 0001 | 00000001 | | MAMMARY GLAND | HE METHOD | FEMALE/31 | | UNNECESSARY |
| 0001 | 00000010 | | MAMMARY GLAND | HE METHOD | FEMALE/31 | | NECESSARY |
| 0001 | 00000011 | | MAMMARY GLAND | HE METHOD | FEMALE/31 | | NECESSARY |
| 0001 | 00000100 | | MAMMARY GLAND | HE METHOD | FEMALE/31 | | NECESSARY |
| ... | ... | ... | ... | ... | ... | ... | ... |
| 000n | 00000001 | | STOMACH | HE METHOD | MALE/42 | | NECESSARY |

| TERMINAL ID 711 | RECEIVED IMAGE NUMBER 712 | HIGH-MAGNIFICATION IMAGE DATA 713 | PORTION 714 | STAINING METHOD 715 | SEX/AGE 716 | FEATURE ANALYSIS RESULT 717 | ANALYSIS RESULT INFORMING DATA 718 |
|---|---|---|---|---|---|---|---|
| 0001 | 00000001 | | MAMMARY GLAND | HE METHOD | FEMALE/31 | | |
| 0001 | 00000010 | | MAMMARY GLAND | HE METHOD | FEMALE/31 | | |
| 0001 | 00000011 | | MAMMARY GLAND | HE METHOD | FEMALE/31 | | |
| 0001 | 00000100 | ... | ... | ... | ... | ... | ... |
| 000n | 00000001 | | STOMACH | HE METHOD | MALE/42 | | |

TISSUE STRUCTURE ANALYSIS DB — 800

PARAMETERS USED IN TISSUE STRUCTURE ANALYSIS

| PORTION (801) | STAINING METHOD (802) | ... (803) | HIGH-MAGNIFICATION IMAGE DATA NECESSARY CONDITION BASED ON TISSUE STRUCTURE ANALYSIS RESULT (804) ||||| NECESSITY OF HIGH-MAGNIFICATION IMAGE (805) |
|---|---|---|---|---|---|---|---|---|
| | | | AVERAGE OF FEATURES (f1 - f10) | VARIANCE OF FEATURES | HISTOGRAM OF FEATURES | ... | POSSIBILITY OF SIGNET RING | OTHERS | |
| MAMMARY GLAND | HE METHOD | | | | | | | | UNNECESSARY |
| MAMMARY GLAND | HE METHOD | | | | | | | | NECESSARY |
| ... | | | | | | | | | ... |
| STOMACH | HE METHOD | | | | | | | | ... |
| ... | | | | | | | | | ... |
| PROSTATE | HE METHOD | | | | | | | | NECESSARY |

FEATURE ANALYSIS DB — 810

PARAMETERS USED IN FEATURE ANALYSIS

| PORTION | STAINING METHOD | ... | CANCER CELL PRESENCE/ABSENCE DETERMINATION CRITERION ||||| PRESENCE/ ABSENCE OF CANCER CELL |
| --- | --- | --- | --- | --- | --- | --- | --- | --- |
| | | | AVERAGE OF FEATURES (F1 - F7) | VARIANCE OF FEATURES | HISTOGRAM OF FEATURES | ... | POSSIBILITY OF SIGNET RING | OTHERS | |
| MAMMARY GLAND | HE METHOD | | | | | | | | ABSENT |
| MAMMARY GLAND | HE METHOD | | | | | | | | PRESENT |
| ... | | | | | | | | | |
| STOMACH | HE METHOD | | | | | | | | ABSENT |
| ... | | | | | | | | | |
| PROSTATE | HE METHOD | | | | | | | | ABSENT |

811  812  813        814                                                     815

| REASSIGNED IMAGE NUMBER | HIGH-MAGNIFICATION IMAGE DATA | LINK INFORMATION | ACCUMULATION DATE & TIME | PORTION | STAINING METHOD | SEX/AGE | ANALYSIS RESULTS | DIAGNOSIS RESULT | TREATMENT METHOD |
|---|---|---|---|---|---|---|---|---|---|
| 00000001 | | | 2010/12/20 | MAMMARY GLAND | HE METHOD | FEMALE/31 | | | |
| 00000002 | | | 2010/12/20 | MAMMARY GLAND | HE METHOD | FEMALE/31 | | | |
| 00000003 | | | 2011/01/10 | MAMMARY GLAND | HE METHOD | FEMALE/31 | | | |
| ... | ... | ... | ... | ... | ... | ... | ... | ... | ... |
| FFFFFFFF | | | 2010/11/30 | STOMACH | HE METHOD | MALE/42 | | | |

FIG. 19

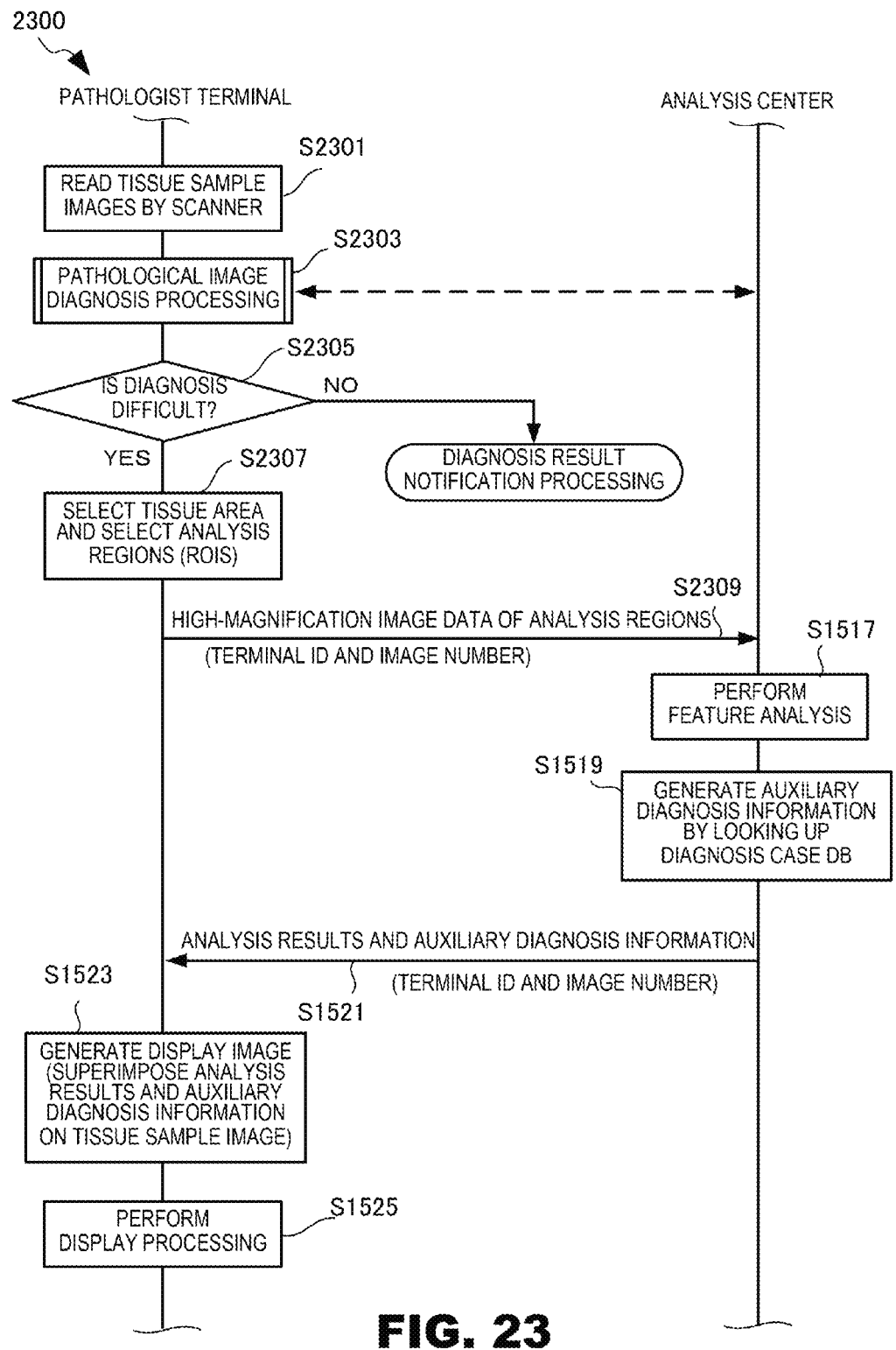

INFORMATION PROCESSING APPARATUS, METHOD, AND STORAGE MEDIUM FOR ASSISTING WITH A DIAGNOSIS BASED ON A TISSUE SAMPLE

CROSS REFERENCE TO RELATED APPLICATIONS

This is a National Stage of International Application No. PCT/JP2012/050249, filed Jan. 10, 2012, claiming priority from Japanese Patent Application No. 2011-012425, filed Jan. 24, 2011, the contents of all of which are incorporated herein by reference in their entirety.

TECHNICAL FIELD

The present invention relates to an information processing technique for assisting diagnosis based on the tissue sample image of a tissue.

BACKGROUND ART

In a technique for assisting diagnosis based on the tissue sample image of a tissue, for example, a cancer cell region is selected from a tissue sample image to analyze features such as the number of cancer cells and provide them to a pathologist. For example, patent literature 1 discloses a diagnosis assistance system which transmits a medical image from a medical image forming system 12 to a specialist in a remote observation station 26, and receives assistance of a diagnosis by him.

CITATION LIST

Patent Literature

Patent literature 1: Japanese PCT National Publication No. 2004-500211 (WO2001/075776)

SUMMARY OF THE INVENTION

Technical Problem

However, when the technique in patent literature 1 is applied to a diagnosis assistance system in which many pathologists request, of a diagnostic center, diagnosis assistance of tissue sample images, they have to wait for the replies of analysis results for a long time because transmission of tissue sample images takes time under the restriction of the transmission capacity. For example, transmitting the tissue sample image of one slide using a general public line sometimes takes several min to 10 min or longer.

The present invention enables to provide a technique of solving the above-described problem.

Solution to Problem

One aspect of the present invention provides an information processing apparatus which assists diagnosis based on a tissue sample image obtained by staining and capturing a tissue, comprising a first receiver that receives lower-magnification image data among a plurality of image data obtained at different magnifications for an area image selected in the tissue sample image;

a first analyzer that analyzes the area image based on the lower-magnification image data received by said first receiver, and generates first feature information;

a determination unit that determines whether analysis based on higher-magnification image data is necessary for the area image, based on the first feature information generated by said first analyzer;

a notification unit that notifies a request of transmitting the higher-magnification image data for the area image, when said determination unit determines that analysis based on the higher-magnification image data is necessary;

a second receiver that receives the higher-magnification image data transmitted in response to the transmission request from said notification unit;

a second analyzer that analyzes the area image based on the higher-magnification image data received by said second receiver, and generates second feature information; and a transmitter that transmits the second feature information generated by said second analyzer.

Another aspect of the present invention provides a method for controlling an information processing apparatus which assists diagnosis based on a tissue sample image obtained by staining and capturing a tissue, comprising a first receiving step of receiving lower magnification image data among a plurality of image data obtained at different magnifications for an area image selected in the tissue sample image;

a first analyzing step of analyzing the area image based on the lower magnification image data received in said first receiving step, and generating first feature information;

a determination step of determining whether analysis based on higher magnification image data is necessary for the area image, based on the first feature information generated in the first analyzing step;

a notification step of notifying a request of transmitting the higher magnification image data for the area image, when analysis based on the higher magnification image data is determined to be necessary in said determination step;

a second receiving step of receiving the higher magnification image data transmitted in response to the transmission request in said notification step;

a second analyzing step of analyzing the area image based on the higher magnification image data received in the second receiving step, and generating second feature information; and a transmitting step of transmitting the second feature information generated in the second analyzing step.

Still other aspect of the present invention provides a non-transitory computer-readable storage medium storing a program for controlling an information processing apparatus which assists diagnosis based on a tissue sample image obtained by staining and capturing a tissue, the control program causing a computer to execute a first receiving step of receiving lower magnification image data among a plurality of image data obtained at different magnifications for an area image selected in the tissue sample image;

a first analyzing step of analyzing the area image based on the lower magnification image data received in said first receiving step, and generating first feature information;

a determination step of determining whether analysis based on higher magnification image data is necessary for the area image, based on the first feature information generated in the first analyzing step;

a notification step of notifying a request of transmitting the higher magnification image data for the area image, when analysis based on the higher magnification image data is determined to be necessary in said determination step;

a second receiving step of receiving the higher magnification image data transmitted in response to the transmission request in said notification step;

a second analyzing step of analyzing the area image based on the higher magnification image data received in the second receiving step, and generating second feature information; and a transmitting step of transmitting the second feature information generated in the second analyzing step.

Still other aspect of the present invention provides an information processing apparatus which requests assistance of diagnosis based on a tissue sample image obtained by staining and capturing a tissue, comprising a first transmitter that transmits lower magnification image data among a plurality of image data obtained at different magnifications for an area image selected in the tissue sample image, in association with transmission source identifying information for identifying the information processing apparatus, and image data identifying information for identifying the image data;

a second transmitter that transmits, in response to a notification of a request of transmitting higher magnification image data among the plurality of image data obtained at different magnifications, the higher magnification image data for the area image in association with the transmission source identifying information and the image data identifying information;

a receiver that receives feature information of the area image associated with the image data identifying information; and a display unit that displaying presence/absence information of the notification of the transmission request for the area image, and the feature information of the area image with distinguishably superimposing them on the tissue sample image.

Still other aspect of the present invention provides a method for controlling an information processing apparatus which requests assistance of diagnosis based on a tissue sample image obtained by staining and capturing a tissue, comprising a first transmitting step of transmitting lower magnification image data among a plurality of image data obtained at different magnifications for an area image of an area selected in the tissue sample image, in association with transmission source identifying information for identifying the information processing apparatus, and image data identifying information for identifying the image data;

a second transmitting step of transmitting, in response to a notification of a request to transmit higher magnification image data among the plurality of image data obtained at different magnifications, the higher magnification image data for the area image in association with the transmission source identifying information and the image data identifying information;

a receiving step of receiving feature information of the area image associated with the image data identifying information; and a displaying step of displaying presence/absence of the notification of the transmission request for the area image, and the feature information of the area image with distinguishably superimposing them on the tissue sample image.

Still other aspect of the present invention provides a non-transitory computer-readable storage medium storing a program for controlling an information processing apparatus which requests assistance of diagnosis based on a tissue sample image obtained by staining and capturing a tissue, the control program causing a computer to execute a first transmitting step of transmitting lower magnification image data among a plurality of image data obtained at different magnifications for an area image of an area selected in the tissue sample image, in association with transmission source identifying information for identifying the information processing apparatus, and image data identifying information for identifying the image data;

a second transmitting step of transmitting, in response to a notification of a request to transmit higher magnification image data among the plurality of image data obtained at different magnifications, the higher magnification image data for the area image in association with the transmission source identifying information and the image data identifying information;

a receiving step of receiving feature information of the area image associated with the image data identifying information; and a displaying step of displaying presence/absence of the notification of the transmission request for the area image, and the feature information of the area image with distinguishably superimposing them on the tissue sample image.

Still other aspect of the present invention provides an information processing system which assists diagnosis based on a tissue sample image obtained by staining and capturing a tissue, comprising a first analyzer that analyzes lower magnification image data among a plurality of image data obtained at different magnifications for an area image selected in the tissue sample image, and generates first feature information of the area image;

a determination unit that determines whether analysis of higher magnification image data is necessary for the area image, based on the first feature information generated by said first analyzer;

a second analyzer that analyzes the area image based on the higher magnification image data, and generates second feature information, when said determination unit determines that analysis of the higher magnification image data is necessary; and a display unit that distinguishably displays a result of the determination by said determination unit and the second feature information generated by said second analyzer.

Still other aspect of the present invention provides an information processing method for assisting diagnosis based on a tissue sample image obtained by staining and capturing a tissue, comprising a first analyzing step of analyzing lower magnification image data among a plurality of image data obtained at different magnifications for the area image selected in the tissue sample image, and generating first feature information of the area image;

a determination step of determining whether analysis of higher magnification image data is necessary for the area image, based on the first feature information generated in said first analyzing step;

a second analyzing step of analyzing the area image based on the higher magnification image data, and generating second feature information, when analysis of the higher magnification image data is determined to be necessary in said determination step; and distinguishably displaying a result of the determination in said determination step and the second feature information generated in said second analyzing step.

Advantageous Effects of Invention

According to the present invention, high-accuracy diagnosis assistance can be quickly provided for a tissue sample image from a pathologist regardless of the restriction of the transmission capacity.

BRIEF DESCRIPTION OF DRAWINGS

FIG. 5A is a view showing an analysis result display screen on the pathologist terminal according to the second embodiment of the present invention;

FIG. 7A is a chart showing the structure of a low-magnification image table according to the second embodiment of the present invention;

FIG. 7B is a chart showing the structure of a high-magnification image table according to the second embodiment of the present invention;

FIG. 8A is a chart showing the structure of a tissue structure analysis DB according to the second embodiment of the present invention;

FIG. 8B is a chart showing the structure of a feature analysis DB according to the second embodiment of the present invention;

FIG. 19 is a chart showing the structure of a diagnosis case DB according to the fourth embodiment of the present invention;

FIG. 23 is a sequence chart showing the operation sequence of an information processing system including an information processing apparatus according to the fifth embodiment of the present invention.

DESCRIPTION OF EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
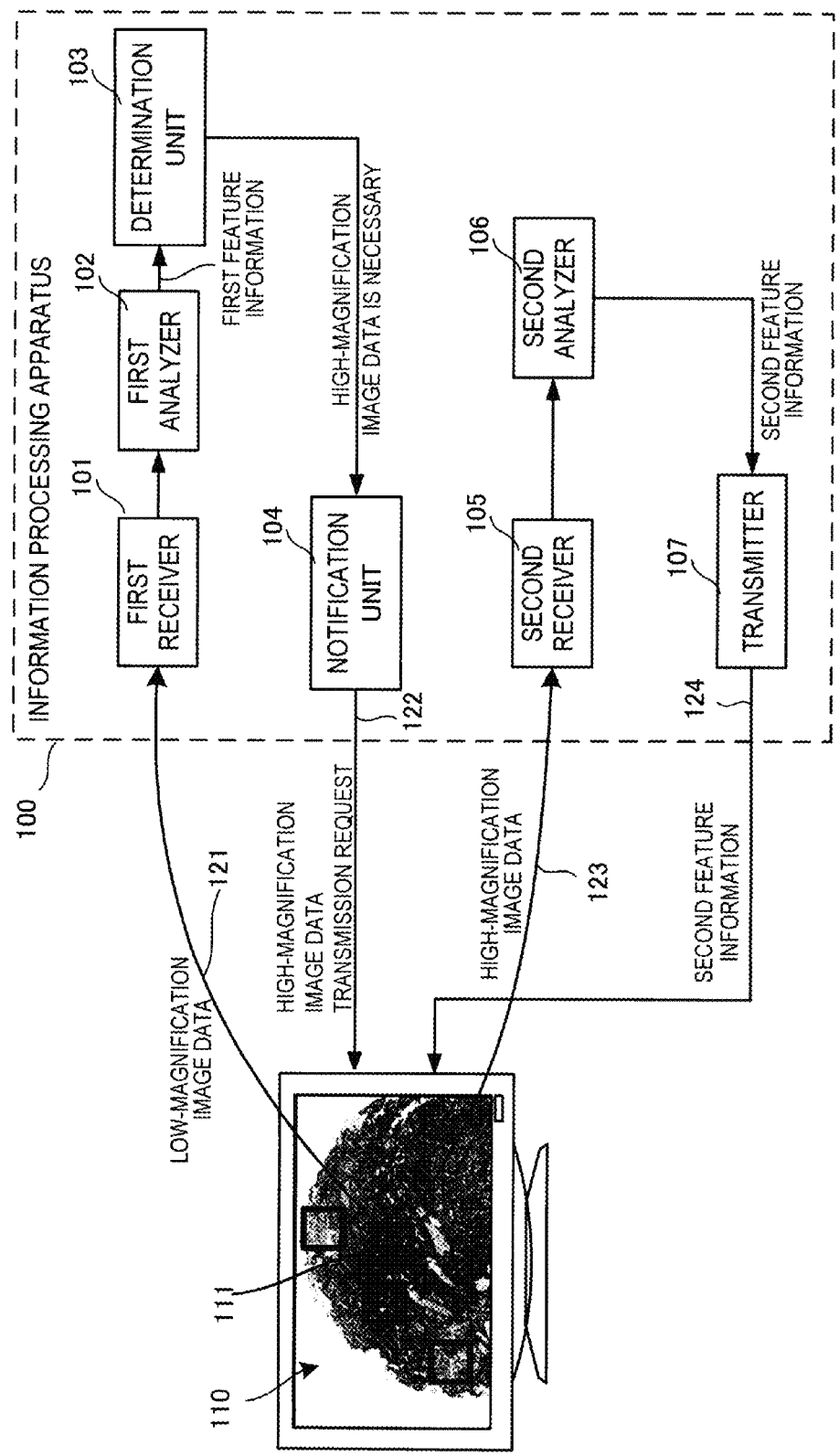
FIG. 1 is a block diagram showing the arrangement of an information processing apparatus according to the first embodiment of the present invention.

An information processing apparatus 100 according to the first embodiment of the present invention will be described with reference to FIG. 1. The information processing apparatus 100 in FIG. 1 is an apparatus which assists diagnosis based on a tissue sample image obtained by staining and capturing a tissue. As shown in FIG. 1, the information processing apparatus 100 includes a first receiver 101, first analyzer 102, determination unit 103, notification unit 104, second receiver 105, second analyzer 106, and transmitter 107.

The first receiver 101 receives lower-magnification image data 121 among a plurality of image data obtained at different magnifications for an area image 111 in a region selected in a tissue sample image 110. The first analyzer 102 analyzes the area image 111 based on the low-magnification image data 121 received by the first receiver 101, and generates first feature information. Based on the first feature information generated by the first analyzer 102, the determination unit 103 determines whether analysis based on higher-magnification image data is necessary for the area image 111. When the determination unit 103 determines that the analysis based on higher-magnification image data is necessary, the notification unit 104 transmits a transmission request 122 for higher-magnification image data of the area image 111. The second receiver 105 receives high-magnification image data 123 transmitted in response to the transmission request 122 from the notification unit 104. The second analyzer 106 analyzes the area image 111 based on the high-magnification image data 123 received by the second receiver 105, and generates second feature information. The transmitter 107 transmits the second feature information 124 generated by the second analyzer 106.

According to the first embodiment, high-accuracy diagnosis assistance can be quickly provided for a tissue sample image from a pathologist regardless of the restriction of the transmission capacity.

Second Embodiment

The second embodiment will describe a pathological image diagnosis assistance system in which a plurality of pathologist terminals and an analysis center are connected via a network, and the analysis center analyzes a tissue sample image transmitted from the pathologist terminal and assists diagnosis. First, the pathologist terminal transmits a low-magnification area image of a selected region. Then, the analysis center analyzes the low-magnification area image, and determines whether it is necessary to analyze a high-magnification area image. If necessary, the analysis center requests the pathologist terminal to transmit a high-magnification area image. The analysis center analyzes the high-magnification area image, and informs the pathologist terminal of the analysis result(s) which assists diagnosis. According to the embodiment, assistance of the analysis center for diagnosis by a pathologist based on a tissue sample image can be quickly received at high accuracy. Also, the diagnosis assistance service in the analysis center can be implemented with a small amount of resources.

<<Arrangement of Information Processing System>>

Figure 2:
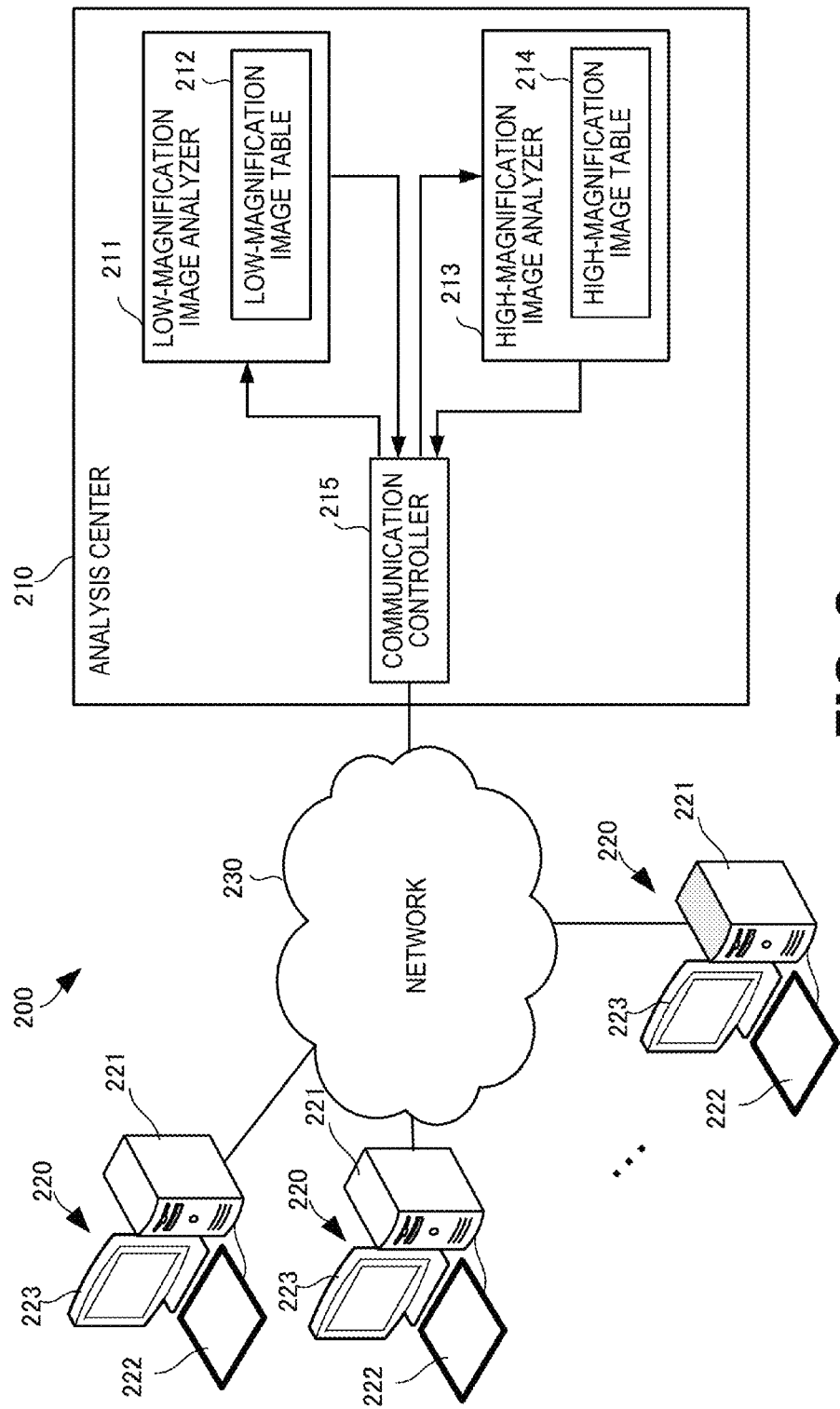
FIG. 2 is a block diagram showing the arrangement of an information processing system including an information processing apparatus according to the second embodiment of the present invention.

FIG. 2 is a chart showing the arrangement of a pathological image diagnosis assistance system 200 serving as an information processing system according to the second embodiment.

The pathological image diagnosis assistance system 200 includes an information processing apparatus functioning as an analysis center 210, information processing apparatuses functioning as a plurality of pathologist terminals 220, and a network 230 which connects the analysis center 210 and the pathologist terminals 220.

The analysis center 210 includes a communication controller 215 for communicating with the plurality of pathologist terminals 220 via the network 230. The analysis center 210 also includes a low-magnification image analyzer 211 which analyzes a low-magnification area image of one region of interest (to be referred to as an ROI hereinafter) transmitted from the pathologist terminal 220, and if necessary as a result of the analysis, requests transmission of a high-magnification area image of the same ROI. The low-magnification image analyzer 211 includes a low-magnification image table 212 used for analysis of a low-magnification area image and a high-magnification area image transmission request. Further, the analysis center 210 includes a high-magnification image analyzer 213 which analyzes a high-magnification area image of the same ROI transmitted from the pathologist terminal 220 and sends back the analysis result as diagnosis assistance information to the pathologist terminal 220. The high-magnification image analyzer 213 includes a high-magnification image table 214 used for analysis of a high-magnification area image and transmission of diagnosis assistance information.

Each pathologist terminal 220 includes a controller 221 which controls the operation of the pathologist terminal 220 and communication with the analysis center 210. The pathologist terminal 220 also includes a scanner 222 which reads, at a resolution corresponding to a high magnification, a pathological slide obtained by capturing a stained tissue. Further, the pathologist terminal 220 includes a display 223 which displays a tissue sample image read by the scanner 222. Assume that necessary input/output devices are connected though FIG. 2 does not illustrate a keyboard, pointing device, or the like for data input and operation instruction.

In the embodiment, the low magnification is "×10", and the high magnification is "×40". When the magnification is expressed by the resolution of a tissue sample image, the low magnification is expressed as 3,000×3,000 pixels, and the high magnification is expressed as 12,000×12,000 pixels. At the low magnification, a tissue structure including the shape of a duct and the like can be analyzed, but each cell or cell nucleus cannot be analyzed. To the contrary, at the high magnification, even each cell and cell nucleus can be analyzed accurately.

<<Operation Sequence of Information Processing System>>

Figure 3:
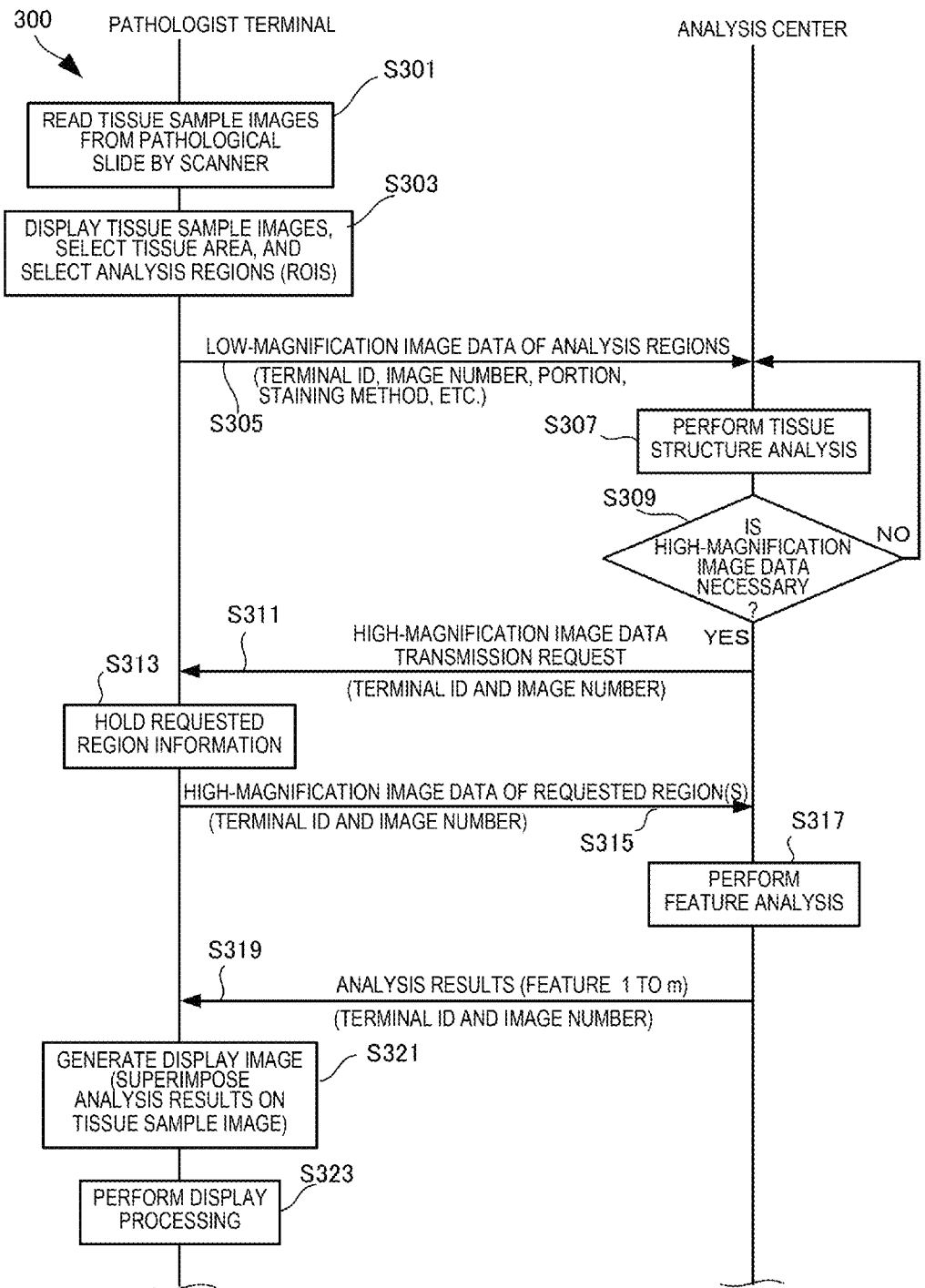
FIG. 3 is a sequence chart showing the operation sequence of the information processing system including the information processing apparatus according to the second embodiment of the present invention.

FIG. 3 is a sequence chart showing an operation sequence 300 of the pathological image diagnosis assistance system 200 serving as the information processing system according to the embodiment. In FIG. 3, an operation from reading of a pathological slide by the scanner 222 of the pathologist terminal 220 up to screen display of diagnosis assistance information will be explained.

First, in step S301, the pathologist terminal 220 reads tissue sample images from a pathological slide by using the scanner 222. The embodiment assumes that the resolution of the scanner 222 corresponds to high-magnification image data of a tissue sample image, but the resolution does not have an upper limit. Then, in step S303, the display 223 displays the read tissue sample images. A tissue area used for diagnosis is selected from a plurality of tissue areas in the tissue sample image. Further, ROIs, analysis of which is requested of the analysis center 210 for diagnosis assistance, are selected from the selected tissue area (see FIG. 4). Note that selection of a tissue area and selection of ROIs may be designated by a pathologist from the tissue sample image on the screen of the display 223, or may be decided by existing automatic ROI-setting software. For example, the automatic ROI-setting software is a light software module which decides target regions by calculation (for example, detection of regions deeply stained in hematoxylin) of a small load, in comparison to a calculation amount for a full-fledged cancer diagnosis which is performed in the analysis center 210. In this specification, this software module will be called LWA (Light-Weight Analyzer).

In step S305, the pathologist terminal 220 transmits low-magnification image data of the selected ROIs to the analysis center 210. In the embodiment, a tissue sample image read by the scanner 222 corresponds to high-magnification image data. Hence, the low-magnification image data is generated by decreasing the resolution by thinning processing or the like. At least the terminal ID of the pathologist terminal 220, an image number for identifying an image, the portion (for example, stomach, lung, breast, or prostate) of the captured tissue, and the staining method (for example, HE method, IHC method, or FISH method) are added to the low-magnification image data to be transmitted, for the purpose of analysis and result transmission by the analysis center 210. The image number is a number independent of personal information of a patient, and is assigned after conversion so that management of the personal information is completed within the pathologist terminal 220. The assignment method will be explained with reference to FIG. 7A. The portion of the tissue and the staining method are associated with each other. If only either information suffices for selection of an analysis method, only this information is used. For example, information of the sex and age, information of the address and nationality, and the like may be added for analysis, or accumulation and analysis of information in a database (to be referred to as a DB hereinafter) as long as personal information of the patient does not leak. Although a plurality of ROIs are generally selected in one tissue area, low-magnification image data may be transmitted at once for a plurality of ROIs or individually for the respective ROIs.

Upon receiving the low-magnification image data, in step S307, the analysis center 210 performs simple tissue structure analysis by using a tissue structure analysis DB which has been registered in advance by machine learning based on low-magnification image data of ROIs. As a result of the tissue structure analysis, in step S309, the analysis center 210 determines whether analysis using high-magnification image data is necessary because this ROI is considered to be a cancer cell candidate. Note that the result of the tissue structure analysis and the result of determining whether analysis using high-magnification image data is necessary sometime change depending on the portion of a tissue and the staining method. FIG. 8A exemplifies the tissue structure analysis DB.

If analysis using high-magnification image data is unnecessary, determination is made for the next ROI. In the embodiment, the area image of each ROI is independently analyzed without associating it with the patient and the transmission source pathologist terminal. Also, the area image of each ROI may be analyzed independently of the area image of another ROI in a tissue sample image obtained from the same pathological slide.

If the analysis center 210 determines that analysis using high-magnification image data is necessary, it requests the pathologist terminal 220 to transmit high-magnification image data in step S311. The transmission request can identify an area image by the transmission source terminal ID and image number without transmitting patient information. The pathologist terminal 220 confirms, from the transmission source terminal ID, that the request partner is the pathologist terminal 220 itself, and specifies high-magnification image data to be transmitted based on the image number. In step S313, to display the analysis results, the pathologist terminal 220 holds ROI information for which high-magnification image data has been requested. In step S315, the pathologist terminal 220 transmits the requested high-magnification image data of the ROI to the analysis center 210 together with the transmission source terminal ID and image number.

Upon receiving the high-magnification image data, in step S317, the analysis center 210 performs fine feature analysis by using a feature analysis DB which has been registered in advance by machine learning based on high-magnification image data of ROIs. Note that the feature analysis sometimes changes depending on the portion of a tissue and the staining method. FIG. 8B exemplifies the feature analysis DB. In step S319, the analysis center 210 transmits, as the analysis results to the pathologist terminal 220, feature analyzed based on the high-magnification image data, or feature information representing the feature.

Figure 5B:
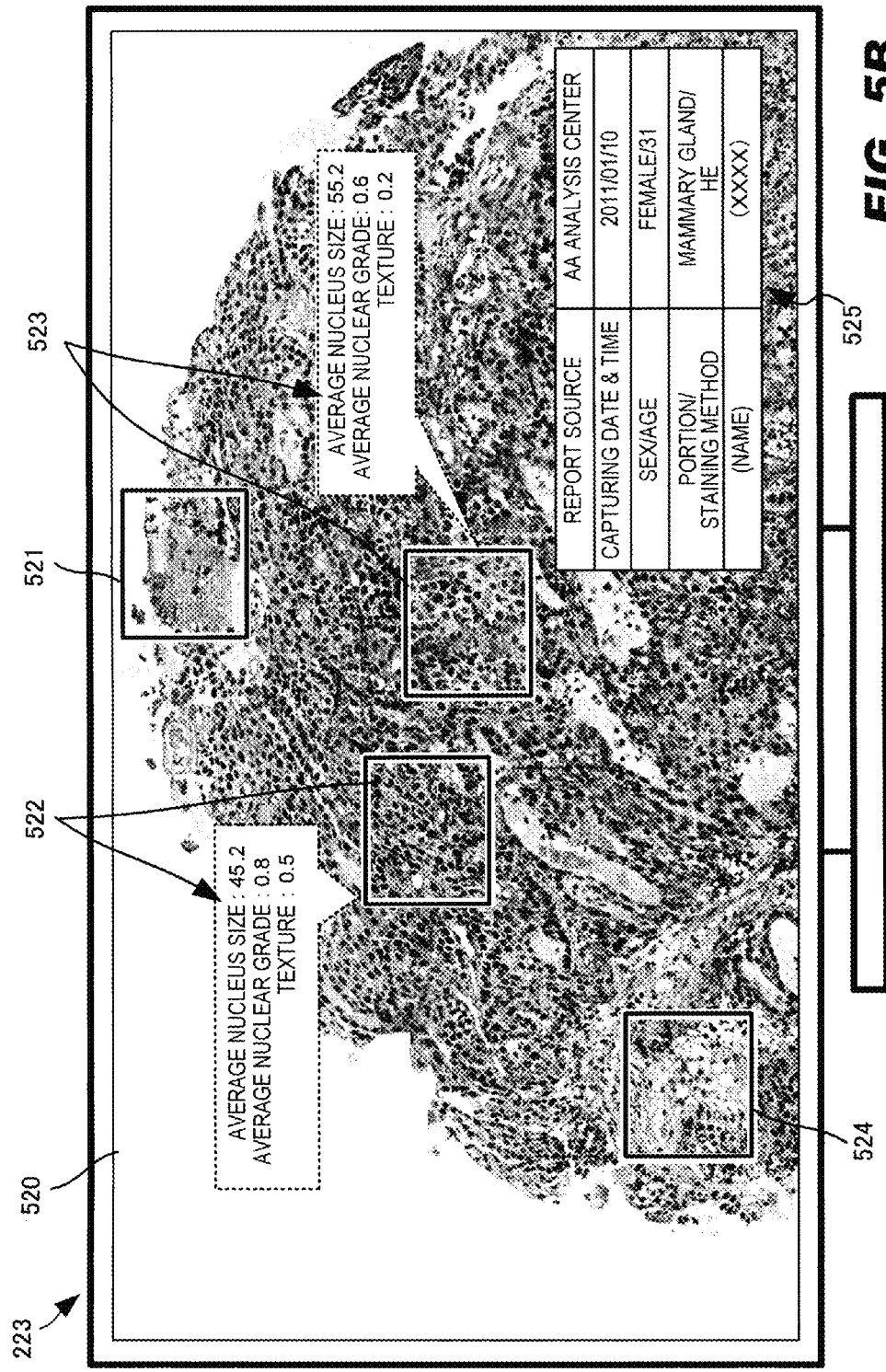
FIG. 5B is a view showing an analysis result display screen on the pathologist terminal according to the second embodiment of the present invention.

Upon receiving the analysis results, the pathologist terminal 220 superimposes in step S321 the analysis results on the tissue sample image read from the pathological slide in step S301, and displays it on the display 223 in step S323 (see FIGS. 5A and 5B). The pathologist diagnoses the tissue sample image by referring to the analysis results displayed on the display 223 as assistance information.

Note that prediction of diagnosis from feature in the feature analysis of step S317 has already been implemented. In this case, a predicted diagnosis may also be displayed on the display 223 to assist diagnosis in step S323.

<<Display Screen on Pathologist Terminal>>

A display screen on the display 223 in processing according to the embodiment will be explained with reference to FIGS. 4, 5A, and 5B.

(Display Screen in Area Image Transmission)

Figure 4:
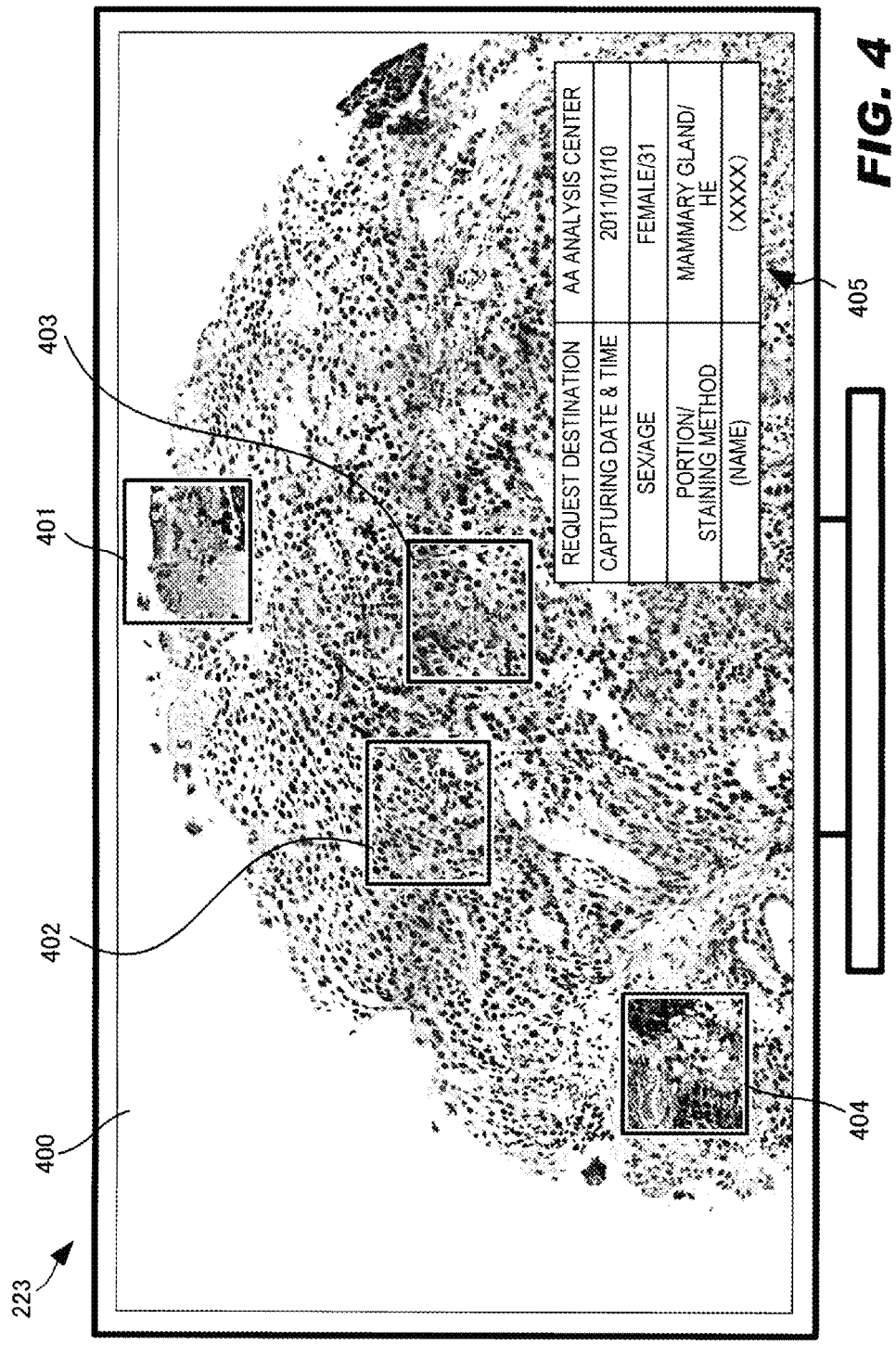
FIG. 4 is a view showing a display screen when transmitting an ROI image from a pathologist terminal according to the second embodiment of the present invention.

FIG. 4 is a view showing a screen 400 displayed on the display 223 of the pathologist terminal 220 when transmitting the area image of a selected ROI to the analysis center 210.

The screen 400 displays a plurality of selected ROIs 401 to 404 which are superimposed on a tissue area selected from a tissue sample image. Low-magnification area images in the ROIs 401 to 404 are transmitted to the analysis center 210 in order to obtain diagnosis assistance information. The area images of the ROIs 401 to 404 may be transmitted at once or sequentially for each ROI. Note that the ROI is rectangular in FIG. 4, but may have another shape such as a circle or ellipse or a shape conforming to the contour of a cluster of cells.

In FIG. 4, information 405 includes management information of the displayed tissue sample image in the pathologist terminal 220, and information for identifying the analysis center 210 as a request destination of which diagnosis assistance is requested. Of these pieces of information, personal information such as the name is not transmitted to the analysis center 210. Note that the information 405 is merely an example, and is not limited to this.

(Analysis Result Display Screen)

FIG. 5A is a view showing a first screen 510 obtained by displaying, on the display 223 of the pathologist terminal 220, the result of analysis based on the low-magnification image data in the analysis center 210.

In FIG. 5A, the analysis results of the ROIs 401 to 404 in FIG. 4 are represented by the difference of the line of a rectangular frame surrounding each ROI. A thin solid line indicates that an ROI 511 is a cancer cell-free area for which no high-magnification image data need be analyzed. Thick solid lines indicate that ROIs 512 and 513 require analysis of high-magnification image data and are areas where cancer cells are obvious. A thick broken line indicates that an ROI 514 requires analysis of high-magnification image data but is a cancer cell-free area. Note that the analysis results are represented by the difference of the line of a rectangular frame in FIG. 5A, but another identifiable display such as the difference of the color is usable.

In FIG. 5A, information 515 includes management information of the displayed tissue sample image in the pathologist terminal 220, and information for identifying the analysis center 210 as a report source which has reported the analysis results for diagnosis assistance. Of these pieces of information, personal information such as the name is managed in the pathologist terminal 220. Note that the information 515 is merely an example, and is not limited to this.

FIG. 5B is a view showing a second screen 520 obtained by displaying, on the display 223 of the pathologist terminal 220, the result of analysis based on the high-magnification image data in the analysis center 210.

In FIG. 5B, the analysis results of the ROIs 401 to 404 in FIG. 4 are represented by display of features analyzed in correspondence with respective ROIs having cancer cells. No display of feature for ROIs 521 and 524 means that the ROIs 521 and 524 are cancer cell-free areas. ROIs 522 and 523 are displayed together with the values of the average nucleus size ($\mu m^2$), the average nuclear grade, and the texture as features. Note that the feature changes depending on the portion of a tissue and the staining method, and an example of the feature is shown in FIG. 8B. The display of FIG. 5B may be displayed in combination with that of FIG. 5A.

In FIG. 5B, information 525 includes management information of the displayed tissue sample image in the pathologist terminal 220, and information for identifying the analysis center 210 as a report source which has reported the analysis results for diagnosis assistance. Of these pieces of information, personal information such as the name is managed in the pathologist terminal 220. Note that the information 525 is merely an example, and is not limited to this.

<<Hardware Arrangement of Analysis Center>>

Figure 6:
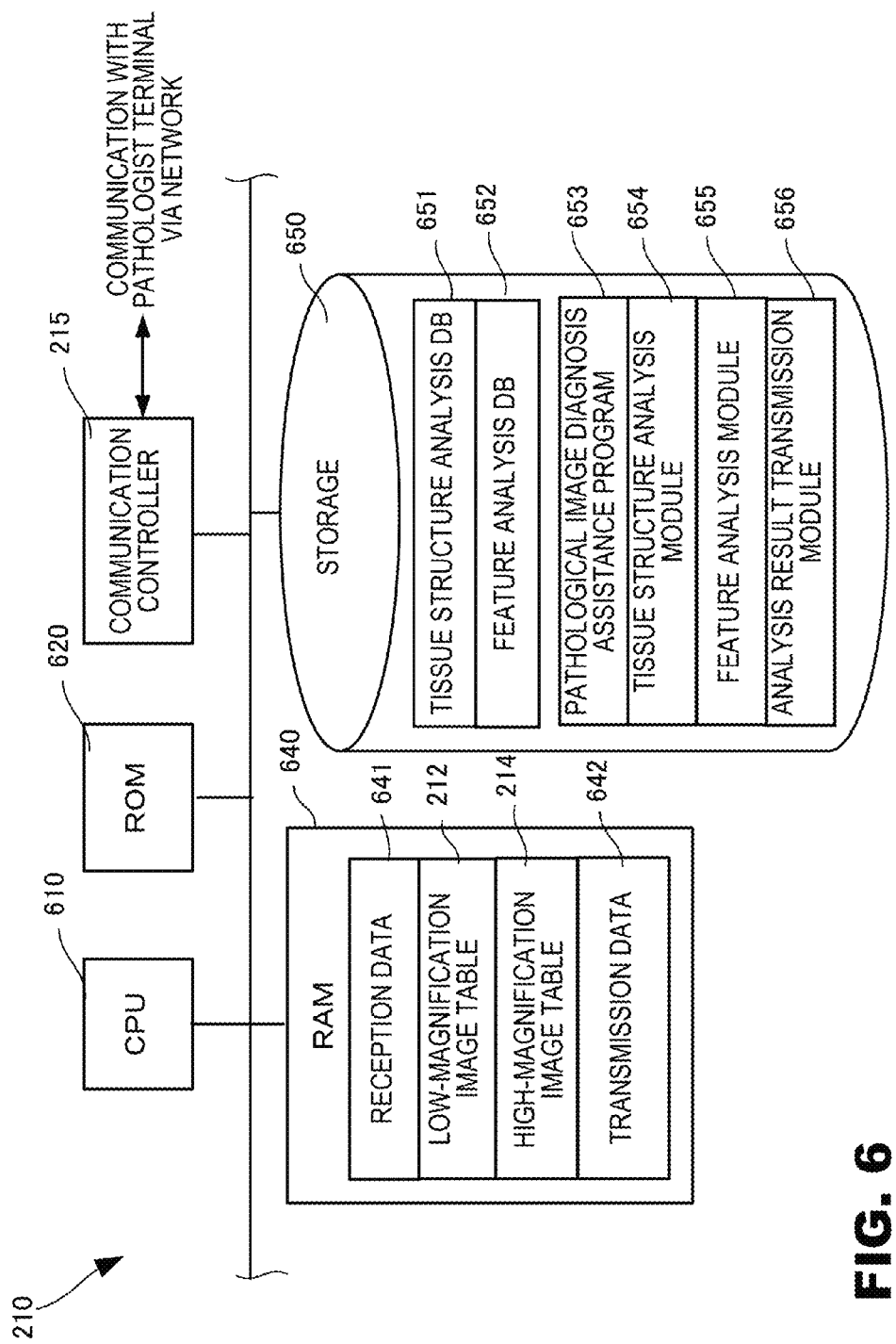
FIG. 6 is a block diagram showing the hardware arrangement of the information processing apparatus according to the second embodiment of the present invention.

FIG. 6 is a chart showing the hardware arrangement of the analysis center 210 according to the embodiment. FIG. 6 shows the arrangement of the analysis center 210 formed from one apparatus, but the analysis center 210 may be formed from a plurality of apparatuses for respective functions.

In FIG. 6, a CPU 610 is an arithmetic control processor, and implements the controller of the analysis center 210 by executing a program. A ROM 620 stores permanent data and programs such as initial data and programs. The communication controller 215 controls communication with the plurality of pathologist terminals 220 via the network 230. This communication is arbitrarily wired or wireless.

A RAM 640 is a random access memory used as a temporary storage work area by the CPU 610. In the RAM 640, areas for storing data necessary to implement the embodiment are ensured. Each area stores reception data 641 including image data of an area image received from the pathologist terminal 220. The RAM 640 stores the low-magnification image table 212 for managing low-magnification image data received from the pathologist terminal 220 (see FIG. 7A). Also, the RAM 640 stores the high-magnification image table 214 for managing high-magnification image data received from the pathologist terminal 220 (see FIG. 7B). Further, the RAM 640 stores transmission data 642 which is to be transmitted to the pathologist terminal 220 and includes analysis results.

A storage 650 is a large-capacity storage device which stores databases, various parameters, and programs to be executed by the CPU 610 in a nonvolatile way. The storage 650 stores the following data or programs necessary to implement the embodiment. As a data storage, the storage 650 stores a tissue structure analysis DB 651 (see FIG. 8A) used to perform tissue structure analysis of an ROI based on low-magnification image data and determine whether analysis of high-magnification image data is necessary. Also, the storage 650 stores a feature analysis DB 652 (see FIG. 8B) used to perform feature analysis of an ROI based on high-magnification image data. Note that the tissue structure analysis DB 651 and feature analysis DB 652 are desirably updated by feedback of image data and analysis results received from the pathologist terminal 220, and learning using statistical processing of analysis results.

Figure 9:
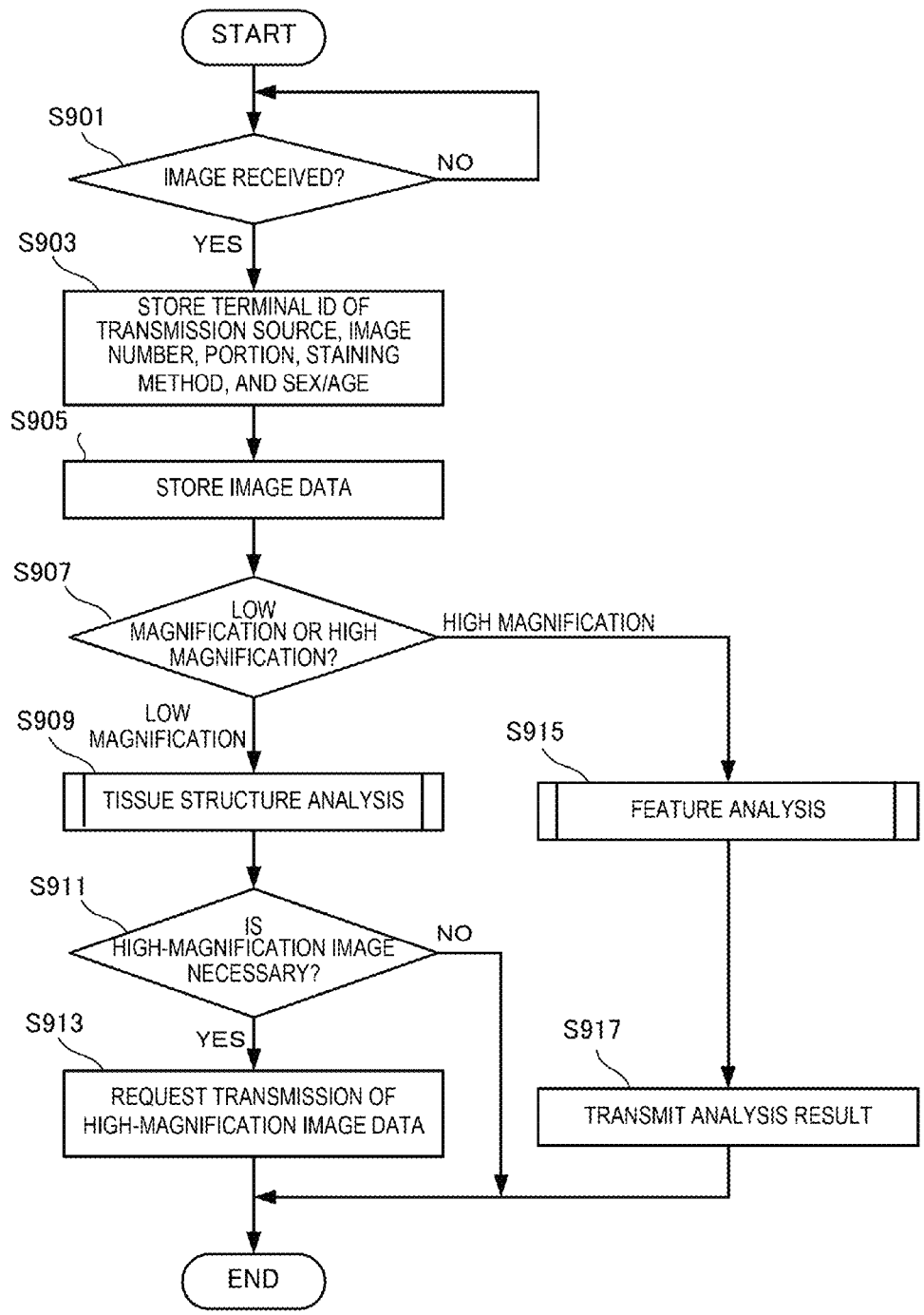
FIG. 9 is a flowchart showing the processing procedure of the information processing apparatus according to the second embodiment of the present invention.

In the embodiment, as a program, the storage 650 stores a pathological image diagnosis assistance program 653 which implements a series of pathological image diagnosis assistances (see FIG. 9). The storage 650 stores a tissue structure analysis module 654 which forms part of the pathological image diagnosis assistance program 653, and performs tissue structure analysis of an ROI based on low-magnification image data by using the tissue structure analysis DB 651. The storage 650 stores a feature analysis module 655 which forms part of the pathological image diagnosis assistance program 653, and performs feature analysis of an ROI based on high-magnification image data by using the feature analysis DB 652. The storage 650 stores an analysis result transmission module 656 which transmits analysis results as diagnosis assistance information to the pathologist terminal 220.

FIG. 6 shows only data and programs necessary for the embodiment, and does not show general-purpose data and programs such as an OS.

(Low-Magnification Image Table)

FIG. 7A is a chart showing the structure of the low-magnification image table 212 in FIGS. 2 and 6 for managing low-magnification image data. The low-magnification image table 212 allows specifying a transmission source transmitted low-magnification image data, and ROIs without personal information, so it is possible to request transmission of high-magnification image data of the same ROIs. All the associations between low-magnification image data and personal information are held in the pathologist terminal 220 and do not leak outside.

The low-magnification image table 212 stores a terminal ID 701 of the pathologist terminal 220 as transmission source identifying information of a transmission source which has transmitted low-magnification image data of an ROI. The low-magnification image table 212 stores, as a received image number 702, an image number serving as image data identifying information assigned by the pathologist terminal 220. In the embodiment, low-magnification image data may be represented by "0" at the most significant bit of the image number 702, but may be represented by another method. The terminal ID 701 and received image number 702 can identify a pathologist terminal 220 and an ROI corresponding to image data in a high-magnification image data transmission request without personal information. Therefore, one number may be used as the terminal ID 701 and received image number 702 for management of image data. The low-magnification image table 212 also stores received low-magnification image data 703. In the low-magnification image data 703, a pointer pointing a storage address of image data stored at another position may be stored.

A portion 704 of a tissue, a staining method 705, and a sex/age 706 are pieces of information for selecting a tissue structure analysis method for the low-magnification image data 703. If the portion or staining method is fixed to one type, these pieces of information are unnecessary. The sex/age 706, and another information for increasing the accuracy of tissue structure analysis may be transmitted from the pathologist terminal 220 in response to a tissue structure analysis accuracy request and referred to, or may not be transmitted. In addition, the low-magnification image table 212 stores a tissue structure analysis result 707 for the low-magnification image data 703, and necessity 708 of a high-magnification image of the same ROI based on the tissue structure analysis result.

(High-Magnification Image Table)

FIG. 7B is a chart showing the structure of the high-magnification image table 214 in FIGS. 2 and 6 for managing high-magnification image data. The high-magnification image table 214 allows specifying a transmission source transmitted high-magnification image data, and ROIs without personal information, and transmitting and managing an analysis result. All the associations between high-magnification image data and personal information are held in the pathologist terminal 220 and do not leak outside.

The high-magnification image table 214 stores a terminal ID 711 of the pathologist terminal 220 serving as a transmission source which has transmitted high-magnification image data of an ROI. The high-magnification image table 214 stores, as a received image number 712, an image number assigned by the pathologist terminal 220. In this case, "1" at the most significant bit of the image number 712 represents high-magnification image data, and if the ROI is the same, a number indicated by lower bits is managed as the same number as the image number 702 in FIG. 7A. The terminal ID 711 and received image number 712 can identify a pathologist terminal 220 and an ROI corresponding to image data in an analysis result based on high-magnification image data without personal information. The high-magnification image table 214 also stores received high-magnification image data 713. In the high-magnification image data 713, a pointer pointing a storage address of image data stored at another position may be stored.

A portion 714 of a tissue, a staining method 715, and a sex/age 716 are pieces of information for selecting a feature analysis method for the high-magnification image data 713. If the portion or staining method is fixed to one type, these pieces of information are unnecessary. The sex/age 716, and another information for increasing the accuracy of feature analysis may be transmitted from the pathologist terminal 220 in response to a feature analysis accuracy request and referred to, or may not be transmitted. In addition, the high-magnification image table 214 stores a feature analysis result 717 for the high-magnification image data 713, and analysis result informing data 718 generated for reference by a pathologist based on the feature analysis result. Note that the analysis result informing data is the feature analysis result itself, the analysis result informing data 718 need not be set separately.

(Tissue Structure Analysis DB)

FIG. 8A is a view showing the structure of the tissue structure analysis DB 651 in FIG. 6. Note that parameters used in tissue structure analysis, calculation of respective features using them, and the like are not a characteristic part of the embodiment and have already been known, so a description thereof will be omitted (see Japanese Patent Laid-Open No. 2006-153742).

Parameters 800 are used for the known tissue structure analysis. Determination conditions 801 to 805 have been registered in advance by machine learning in order to determine the high-magnification image necessity 708 based on the tissue structure analysis result 707 in FIG. 7A. The determination conditions change depending on the characteristics of a tissue sample image itself such as the portion 801 of a tissue to be analyzed, the staining method 802, and the others 803. The high-magnification image data necessary condition 804 based on the tissue structure analysis result includes high-magnification image data necessary condition parameters obtained in advance from a tissue structure analysis result. These values may be thresholds or define ranges. These determination conditions are conditions to determine whether the ROI is suspected of having cancer. If even one condition is satisfied, it may be determined that the ROI has a cancer, or if a plurality of conditions are satisfied, it may be determined that the ROI has a cancer.

Features analyzed in tissue structure analysis using the HE staining method will be simply explained, but the features are not limited to the following description. As feature, special feature is sometimes used depending on a target organ. However, the following features are important features for cancer at almost all portions. f1 to f10 shown in FIG. 8A are as follows:
f1) nucleus size
f2) density of large nuclei=number of large nuclei/total number of nuclei
f3) density of nuclei belonging to a duct
f4) nucleus orientation
f5) nucleus flatness
f6) duct thickness
f7) color (RGB)
f8) color (HSV)
f9) duct region
f10) signal (orientation feature and alignment) filtered by the Gabor function As a global feature, information about the region such as the mucus or fat is sometimes used in addition to the above features. As special feature, for example, there is a suspected signet ring cell (to be referred to as a signet ring hereinafter) in gastric biopsy.

In actual condition judgment, the above features are used as basic features, and derivatively obtained statistical amounts such as the average, variance, median, quartile, and histogram P-percentile (for example, P=5, 25, 50, 75, 95) are calculated for each ROI and used as the features of the ROI.

If one or a combination of these conditions satisfies a condition that the ROI has a cancer, "necessary" is copied from the high-magnification image necessity 805 to the high-magnification image necessity 708 in the low-magnification image table 212 to request high-magnification image data and perform more detailed feature analysis.

(Feature Analysis DB)

FIG. 8B is a view showing the structure of the feature analysis DB 652 in FIG. 6. Note that parameters used in feature analysis, calculation of respective features using them, and the like are not a characteristic part of the embodiment and have already been known, so a description thereof will be omitted (see Japanese Patent Laid-Open No. 2006-153742).

Parameters 810 are used in the known feature analysis. Determination criteria 811 to 815 have been registered in advance by machine learning in order to generate the analysis result informing data 718 from the feature analysis result 717 in FIG. 7B. The determination criteria change depending on the characteristics of a tissue sample image itself such as the portion 811 of a tissue to be analyzed, the staining method 812, and the others 813. The cancer cell presence/absence determination criterion 814 includes cancer cell presence/absence determination condition parameters obtained in advance from a feature analysis result. These values may be thresholds or define ranges. These judgment conditions are conditions to judge whether the ROI has been suspected of having a cancer and is concluded to have a cancer, or the ROI has been suspected of having a cancer and is concluded to have a benign disease. If even one condition is satisfied, it may be judged that the ROI has a cancer, or if a plurality of conditions are satisfied, it may be judged that the ROI has a cancer.

Features analyzed in feature analysis using the HE staining method will be simply explained, but the features are not limited to the following description. As feature, special feature is sometimes used depending on a target organ. However, the following features are important features for cancer at almost all portions. F1 to F7 shown in FIG. 8B are as follows:
F1) nucleus size
F2) major and minor axes of a nucleus
F3) circularity (it takes a maximum value of 1 as the shape is almost a circle, and a smaller value as the shape deviates from a circle)
F4) texture
F5) color (RGB)
F6) color (HSV)
F7) duct region As special feature, for example, the presence/absence of a signet ring is confirmed based on high-magnification image data when there is a suspected signet ring cell (to be referred to as a signet ring hereinafter) in gastric biopsy based on low-magnification image data.

In actual condition judgment, the above features are used as basic features, and derivatively obtained statistical amounts such as the average, variance, median, quartile, and histogram P-percentile (for example, P=5, 25, 50, 75, 95) are calculated for each ROI and used as the features of the ROI.

If one or a combination of these conditions satisfies a condition that the ROI has a cancer, the result is copied to the presence/absence 815 of a cancer cell, and transmitted to the transmission source of the tissue sample image for diagnosis assistance.

Note that features of the same name used in analysis of low-magnification image data and analysis of high-magnification image data are not equal because the resolutions of the images are different. For example, in analysis of low-magnification image data, the nuclear size is roughly analyzed by extracting a region stained in hematoxylin, and classifying nuclei into large and small ones based on the pixel size. To the contrary, in analysis of high-magnification image data, the contour of a nucleus is accurately extracted to calculate the size (or circularity or the like) based on the contour.

Global information such as a duct is obtained at only a low magnification. For this reason, first, a duct region is extracted to generate a duct mask in analysis of low-magnification image data, and the mask information is directly transferred to the high-magnification image data analysis module. Based on this information, the high-magnification image data analysis module checks whether the duct contains a nucleus to be analyzed, and if the duct contains a nucleus to be analyzed, determines that this nucleus is not a cancer even if its size is large.

The analysis of low-magnification image data and the analysis of high-magnification image data do not have a simple primary analysis-secondary analysis relationship, but a detailed description thereof will be omitted in the embodiment for brevity.

<<Operation Procedure of Analysis Center>>

FIG. 9 is a flowchart showing the operation procedure of the analysis center 210. The CPU 610 in FIG. 6 executes this flowchart by using the RAM 640, thereby implementing the function of the analysis center 210 in FIG. 2.

First, in step S901, the analysis center 210 waits for reception of an image from the pathologist terminal 220. If the analysis center 210 receives an image, the process advances to step S903, and the analysis center 210 stores and holds information including the terminal ID of the transmission source of the received image data, the image number, the portion, the staining method, and the sex/age. In step S905, the analysis center 210 stores and holds the transmitted image data. In the embodiment, which of low-magnification image data and high-magnification image data is the received image data is discriminated from the image number, and the pieces of information stored and held in steps S903 and S905 are stored in the low-magnification image table 212 of FIG. 7A or the high-magnification image table 214 of FIG. 7B.

In step S907, the process branches in correspondence with the discrimination of which of low-magnification image data and high-magnification image data is the received image data. If the received image data is low-magnification image data, the process advances to step S909, and the analysis center 210 performs tissue structure analysis of the low-magnification image data corresponding to the portion, staining method, sex/age, and the like. In the tissue structure analysis performed here, for example, for an HE-stained tissue of a stomach, screening of cancer candidate regions is performed based on disturbance of a duct shape using a known InfoMax algorithm, or the like. In step S911, the analysis center 210 judges, from the result of the tissue structure analysis, whether analysis of high-magnification image data of the same ROI is necessary. If analysis of a high-magnification image of the same ROI is necessary, the process advances to step 913, and the analysis center 210 requests the pathologist terminal 220 serving as the transmission source to transmit high-magnification image data of the same ROI.

If the received image data is high-magnification image data, the process advances to step S915, and the analysis center 210 performs feature analysis of the high-magnification image data corresponding to the portion, staining method, sex/age, and the like. In the feature analysis performed here, for example, for an HE-stained tissue of a stomach, the dimensions and shape of a cell nucleus are analyzed using a known SVM algorithm. In step S917, the analysis center 210 transmits the feature analysis result of the high-magnification image data to the pathologist terminal 220 serving as the transmission source together with the image number obtained from the transmission source.

<<Hardware Arrangement of Pathologist Terminal>>

Figure 10:
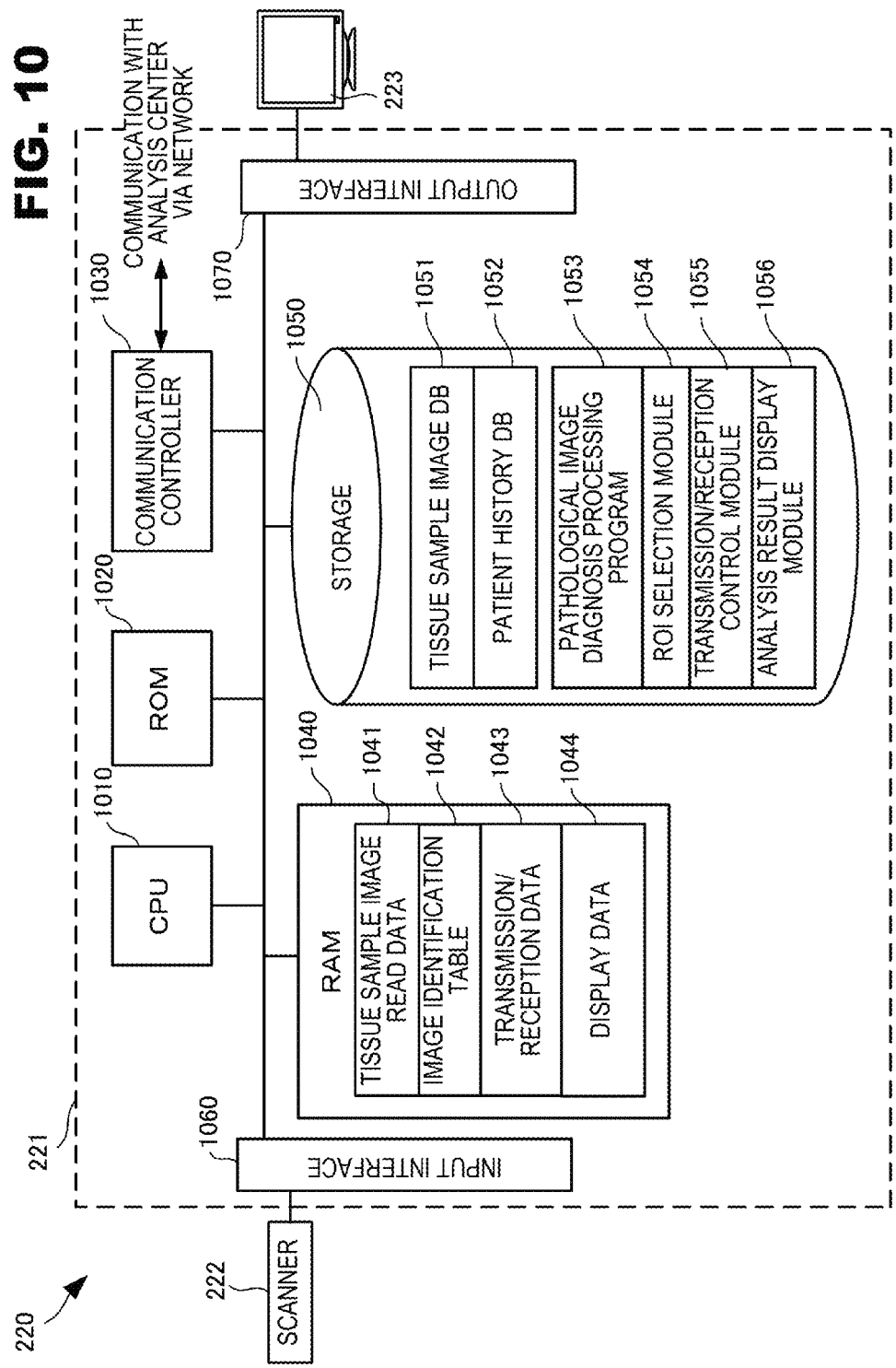
FIG. 10 is a block diagram showing the hardware arrangement of the pathologist terminal according to the second embodiment of the present invention.

FIG. 10 is a chart showing the hardware arrangement of the pathologist terminal 220 according to the embodiment. As shown in FIG. 2, the pathologist terminal 220 includes the controller 221, scanner 222, and display 223 as basic components.

In FIG. 10, a CPU 1010 is an arithmetic control processor, and implements the controller of the pathologist terminal 220 by executing a program. A ROM 1020 stores permanent data and programs such as initial data and programs. A communication controller 1030 controls communication with the analysis center 210 via the network 230. This communication is arbitrarily wired or wireless.

A RAM 1040 is a random access memory used as a temporary storage work area by the CPU 1010. In the RAM 1040, areas for storing data necessary to implement the embodiment are ensured. Each area stores tissue sample image read data 1041 read from a pathological slide by the scanner 222. The RAM 1040 stores an image identification table 1042 for managing low-magnification image data and high-magnification image data to be transmitted to the analysis center 210, and specifying a patient, portion, ROI, and the like (see FIG. 11). Also, the RAM 1040 stores transmission/reception data 1043 to be transmitted to and received from the analysis center 210 (see FIG. 11). Further, the RAM 1040 stores display data 1044 to be displayed on the display 223 of the pathologist terminal 220.

A storage 1050 is a large-capacity storage device which stores databases, various parameters, and programs to be executed by the CPU 1010 in a nonvolatile way. The storage 1050 stores the following data or programs necessary to implement the embodiment. As a data storage, the storage 1050 stores a tissue sample image DB 1051 which is obtained by reading by the scanner 222 and is locally accumulated by a pathologist. Also, the storage 1050 stores a patient history DB 1052 which holds a diagnosis history corresponding to a patient. In a system which intensively accumulates and manages information necessary for the analysis center 210, which will be described in the fourth embodiment, it is only necessary that the tissue sample image DB 1051 and patient history DB 1052 of the pathologist terminal 220 store parameters allowing access to information in the analysis center 210 from the pathologist terminal 220.

Figure 12:
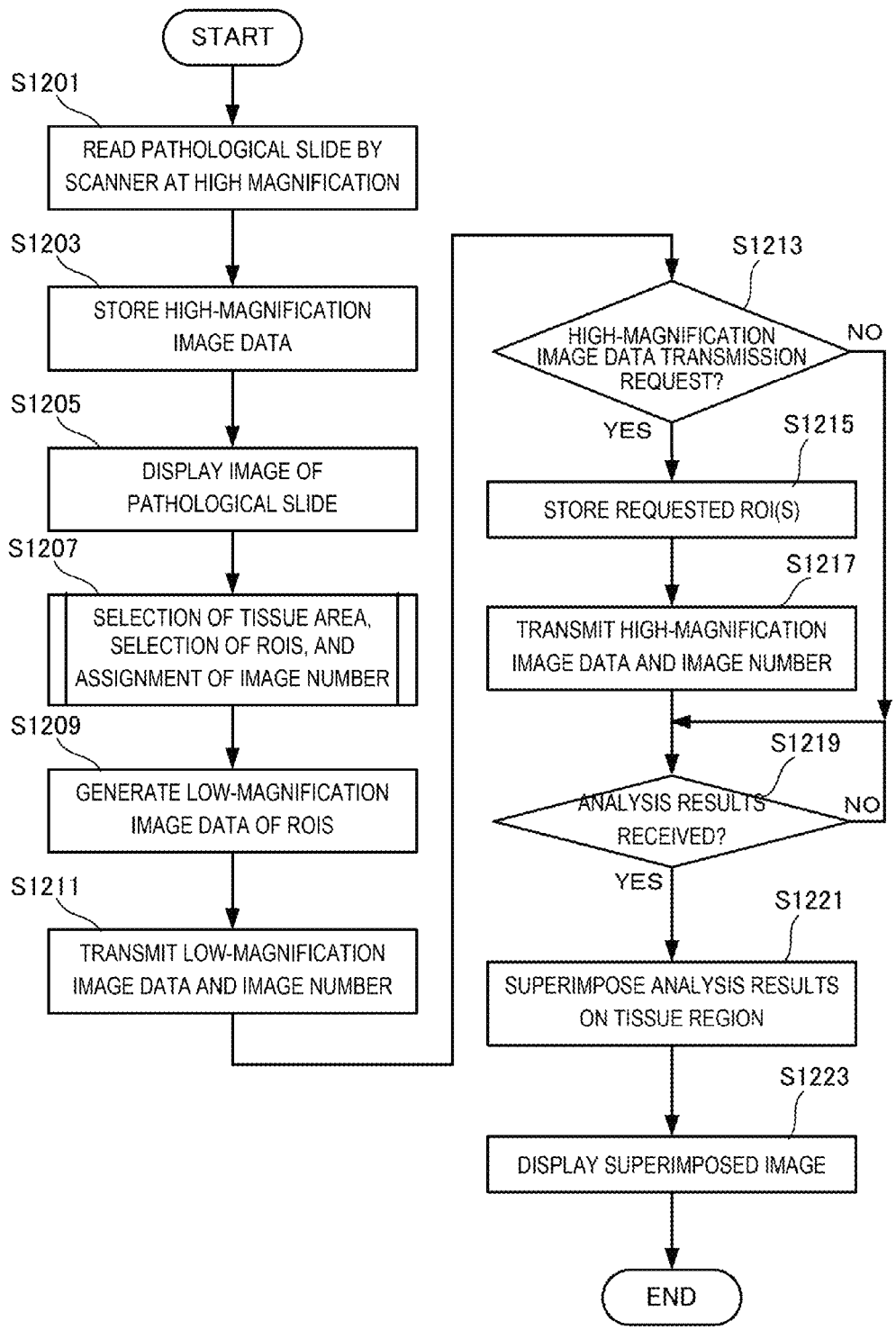
FIG. 12 is a flowchart showing the processing procedure of the pathologist terminal according to the second embodiment of the present invention.

In the embodiment, as a program, the storage 1050 stores a pathological image diagnosis processing program 1053 including processing to request pathological image diagnosis assistance of the analysis center 210 (see FIG. 12). The storage 1050 stores an ROI selection module 1054 which forms part of the pathological image diagnosis processing program 1053, and selects a tissue area and ROIs to be diagnosed from a tissue sample image. The storage 1050 stores a transmission/reception control module 1055 which forms part of the pathological image diagnosis processing program 1053, and controls data communication with the analysis center 210. The storage 1050 stores an analysis result display module 1056 which superimposes and displays, on a tissue sample image, analysis results received from the analysis center 210.

An input interface 1060 is an interface which inputs control signals and data necessary for control by the CPU 1010. In the embodiment, the input interface 1060 inputs image data of a tissue sample image obtained by reading a pathological slide by the scanner 222. Note that a keyboard, pointing device, and the like are not illustrated. An output interface 1070 is an interface which outputs control signals and data to a device under the control of the CPU 1010. In the embodiment, the output interface 1070 outputs a tissue sample image to the display 223, diagnosis assistance request information to the analysis center 210, or analysis results transmitted from the analysis center 210.

FIG. 10 shows only data and programs necessary for the embodiment, and does not show general-purpose data and programs such as an OS.

(Image Identification Table and Transmission/Reception Data)

Figure 11:
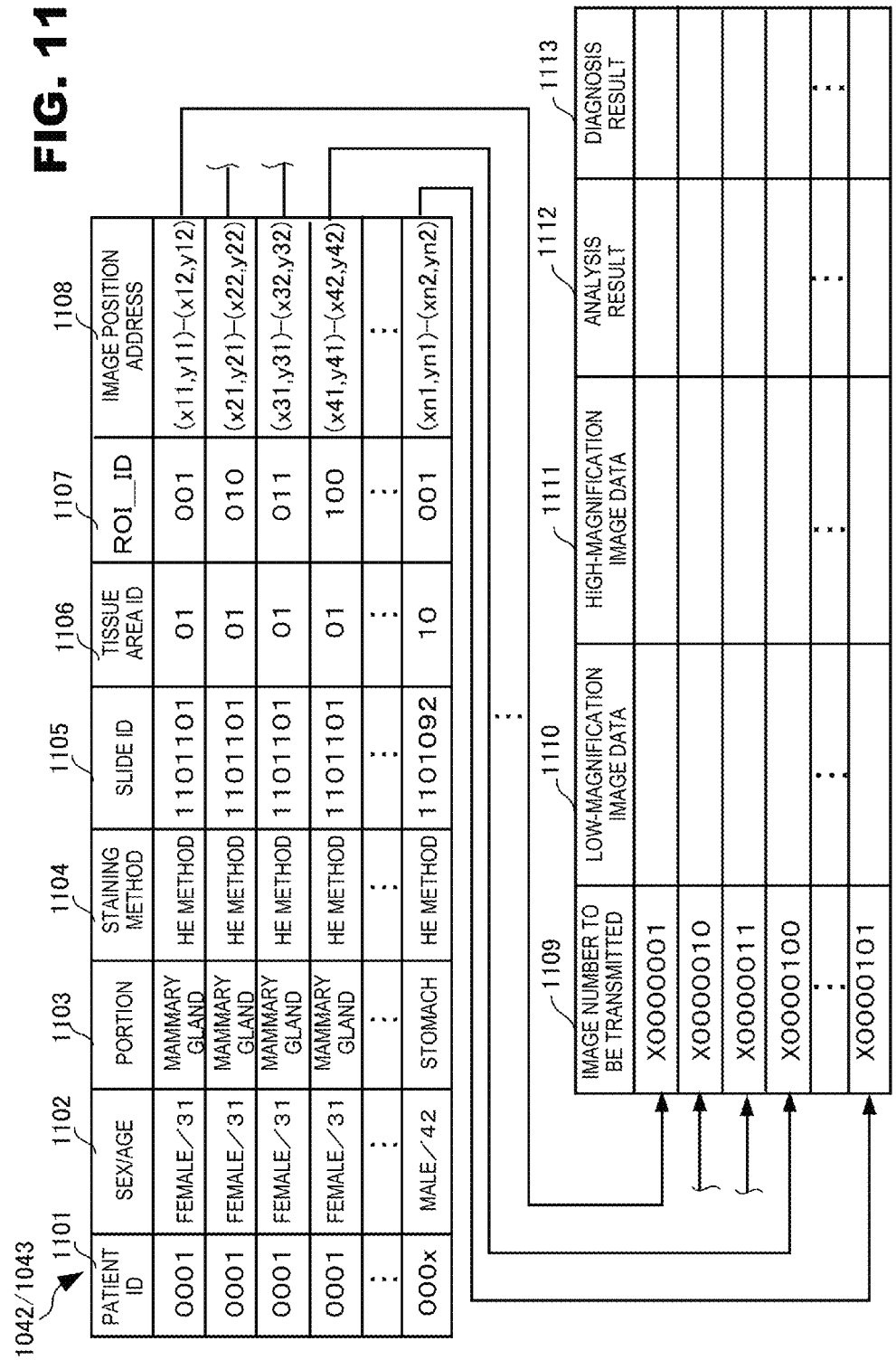
FIG. 11 is a chart showing the structures of an image identification table and transmission/reception data according to the second embodiment of the present invention.

FIG. 11 is a chart showing the structures of the image identification table 1042 and transmission/reception data 1043 shown in FIG. 10.

Reference numeral 1101 denotes a patient ID for identifying a patient; and 1102, a sex/age of a patient that is information for specifying a patient. Although another specifying information such as the address of a patient is also stored, FIG. 11 shows only information necessary for processing in the embodiment. Reference numeral 1103 denotes a portion of a tissue sample image to be analyzed; and 1104, a staining method of the tissue that is information associated with an analysis method in the analysis center 210.

Reference numeral 1105 denotes a slide ID for identifying a pathological slide; 1106, a tissue area ID for identifying a tissue area to be analyzed in a tissue sample image read from a pathological slide by the scanner 222; and 1107, an ROI_ID for identifying an ROI to be analyzed in an area. In the embodiment, upper left and lower right position addresses of a rectangle representing the ROI_ID 1107 in a tissue sample image are stored in 1108. Note that position storage data changes depending on the ROI shape.

In the embodiment, of the data 1101 to 1108, information associated with an analysis method in the analysis center 210 is transmitted to the analysis center 210, but the remaining information about personal information of a patient is not transmitted to the analysis center 210. That is, a unique image number 1109 which is not associated with personal information of a patient and is to be transmitted from the pathologist terminal 220 is assigned to the image of an ROI specified by the data 1101 to 1108.

Reference numeral 1110 denotes low-magnification image data of an ROI specified by the image number 1109 to be transmitted; and 1111, high-magnification image data of the ROI specified by the image number 1109 to be transmitted. Further, an analysis result 1112 reported from the analysis center 210, and a result 1113 of a diagnosis made by a pathologist by referring to the analysis result 1112 as assistance information are stored.

As is apparent from FIGS. 11, 7, and 8, communication of the image data and analysis result of an ROI between the pathologist terminal 220 and the analysis center 210 is basically performed using image information which is not associated with personal information of a patient and is assigned by the pathologist terminal 220.

<<Operation Procedure of Pathologist Terminal>>

FIG. 12 is a flowchart showing the operation procedure of the pathologist terminal 220 according to the embodiment. The CPU 1010 in FIG. 10 executes this flowchart by using the RAM 1040, thereby implementing the function of the pathologist terminal 220 in FIG. 2.

First, the pathologist terminal 220 reads a pathological slide by the scanner 222 at a resolution corresponding to the high magnification in step S1201, and stores the read high-magnification image data in step S1203. In step S1205, the pathologist terminal 220 displays a tissue sample image corresponding to the pathological slide on the display 223. In step S1207, a tissue area as an analysis request target is selected from the tissue sample image corresponding to the pathological slide, an ROI is selected from the tissue area, and an image number is assigned to the image of the ROI. Note that the processing in step S1207 may be automatically performed by the LWA installed in the pathologist terminal 220, or may be performed by interaction with a pathologist using a touch panel on the display screen. An example in which a plurality of ROIs selected to request analysis are superimposed and displayed on the selected tissue area as a result of the processing in step S1207 corresponds to FIG. 4.

In step S1209, the pathologist terminal 220 generates low-magnification image data of the selected ROI. The low-magnification image data generation method can be an existing method and, for example, thinning processing is easy. For conversion from the magnification (×40) into the magnification (×10) in the embodiment, three pixels are thinned out. In step S1211, the pathologist terminal 220 transmits the generated low-magnification image data to the analysis center 210 together with the assigned image number. Note that the terminal ID for identifying the pathologist terminal 220, and information associated with the analysis method in the analysis center 210 are also transmitted together.

In step S1213, the pathologist terminal 220 judges whether the analysis center 210 requests transmission of high-magnification image data of the same ROI. If there is a high-magnification image data transmission request, the process advances to step S1215, and the pathologist terminal 220 stores and holds the requested ROI(s) for display of the analysis result(s). In step S1217, the pathologist terminal 220 transmits high-magnification image data of the requested ROI to the analysis center 210 together with the image number. If there is no high-magnification image data transmission request, the process advances to step S1219.

In step S1219, the pathologist terminal 220 waits for reception of analysis results from the analysis center 210. If the pathologist terminal 220 receives analysis results, the process advances to step S1221, and the pathologist terminal 220 generates a display screen by superimposing the analysis results as numerical data (see FIG. 5B) on the tissue area to be analyzed, or by generating display data in the ROI frame color corresponding to the analysis results (see FIG. 5A) and superimposing them on the tissue area to be analyzed. In step S1223, the pathologist terminal 220 displays the generated display screen on the display 223 to assist diagnosis by the pathologist.

Third Embodiment

In the second embodiment, analysis targets in the analysis center 210 are limited to ROIs in one tissue area selected from the tissue sample image of a pathological slide. In the third embodiment, feature analysis is performed by referring to even ROIs in another tissue area of the same pathological slide. According to the third embodiment, even when analysis of only a selected tissue area is insufficient for diagnosis, assistance of the analysis center for diagnosis by a pathologist based on a tissue sample image can be quickly received at high accuracy.

The arrangements of an information processing system, analysis center, and pathologist terminal according to the third embodiment are similar to those in the second embodiment and can be inferred, so a description thereof will not be repeated.

<<Operation Sequence of Information Processing System>>

Figure 13:
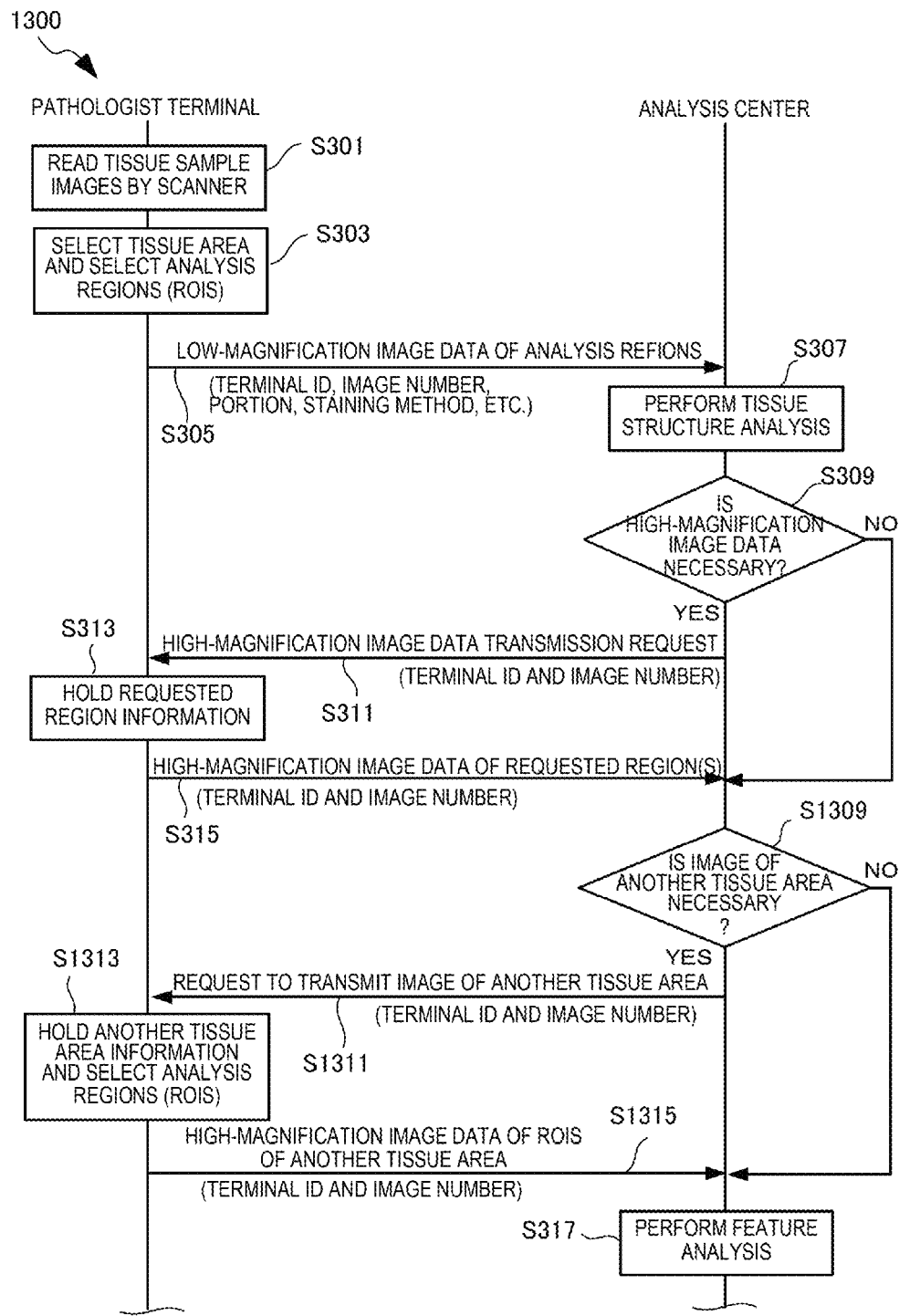
FIG. 13 is a sequence chart showing the operation sequence of an information processing system including an information processing apparatus according to the third embodiment of the present invention.

FIG. 13 is a sequence chart showing an operation sequence 300 of a pathological image diagnosis assistance system 200 serving as the information processing system according to the embodiment. In FIG. 13, an operation from reading of a pathological slide by a scanner 222 of a pathologist terminal 220 up to feature analysis by an analysis center 210 will be explained. An operation (steps S319 to S323) after the feature analysis is the same as that in FIG. 3 of the second embodiment, and a description thereof will not be repeated.

Processes in steps S301 to S315 are the same as those in FIG. 3 of the second embodiment. Whether high-magnification image data is necessary is determined by tissue structure analysis of low-magnification image data of an ROI. If necessary, the analysis center 210 requests the pathologist terminal 220 to transmit high-magnification image data.

In the third embodiment, if no high-magnification image data is necessary (NO in step S309) or after high-magnification image data is transmitted (step S315), it is determined in step S1309 whether analysis of an image of another tissue area is necessary for diagnosis assistance.

For example, it is generally designed to, when a region suspected to have a cancer is detected in analysis of low-magnification image data (10×), select eight region images from the region of the low-magnification image and analyze them based on high-magnification image data. If the number of regions suspected to have a cancer in the tissue area is smaller than eight, a region suspected to have a cancer needs to be further selected from another tissue area. Note that "eight regions" are empirically decided, and the number of regions is not always limited to eight. Since analysis of high-magnification image data takes time, the number of regions is decided by taking account of the tradeoff between accuracy and time. The criterion to select eight regions is, for example, the nuclear density of a region determined to have a cancer in analysis of low-magnification image data, and regions having higher densities are preferentially selected.

When an image of another tissue area is analyzed remotely, transmitting all eight regions via the network is inefficient, so the following processing is desirably performed. First, high-magnification image data of one region is transmitted and analyzed. If the presence of a cancer is determined, transmission of high-magnification image data ends, the final determination is a cancer, and the processing ends. If the absence of a cancer is determined in analysis of the high-magnification image data, the next high-magnification image data is requested to continue the analysis. If cancer is denied in analysis of all the eight high-magnification image data, the final determination is "benign". According to this data transfer method, the processing ends when the presence of a cancer is determined. Thus, all eight high-magnification image data need not be transmitted, the data transfer amount is decreased, and the total diagnosis time is shortened. The same effect is obtained even when eight regions exist in an initially requested tissue area.

If analysis of a selected tissue area is sufficient without analyzing another tissue area, the process advances to step S317 to perform feature analysis based on high-magnification image data. If analysis of another tissue area is necessary, the analysis center 210 requests, of the pathologist terminal 220, an image of another tissue area in step S1311. In step S1313, the pathologist terminal 220 selects another tissue area in accordance with the request, holds the selected information, and selects an ROI from the tissue area. In step S1315, the pathologist terminal 220 transmits high-magnification image data of the ROI of the selected tissue area to the analysis center 210.

In the feature analysis of step S317, the analysis center 210 performs analysis of image data of ROIs of another tissue area requiring additional analysis, in addition to analysis of image data of ROIs selected first. This analysis results are also displayed as diagnosis assistance information on the pathologist terminal 220. FIG. 13 shows, as separate processes, request and transmission of high-magnification image data of ROIs selected first, and those of high-magnification image data of ROIs of another tissue area requiring additional analysis. However, these high-magnification image data may be requested and transmitted simultaneously.

Fourth Embodiment

In the second and third embodiments, the analysis center 210 only informs the pathologist terminal 220 of, as diagnosis assistance information, the analysis results of image data of ROIs sent from the pathologist terminal 220. In the fourth embodiment, an analysis center 1410 accumulates, as a case DB, image data of ROIs which have been analyzed so far for diagnosis assistance, and diagnosis results made by pathologists who referred to the analysis results. When informing a pathologist terminal 220 of an analysis results, the analysis center 1410 further informs it of reference data based on the case DB. According to the embodiment, assistance of the analysis center for diagnosis by a pathologist based on a tissue sample image can be quickly received at high accuracy in consideration of not only judgment by one pathologist but also the learning results of the relationships between tissue sample images, analysis results, and diagnosis results by many pathologists. Further, the pathologist terminal 220 can always refer to diagnosis cases, reducing the necessity to manage past diagnosis cases in the pathologist terminal 220.

<<Arrangement of Information Processing System>>

Figure 14:
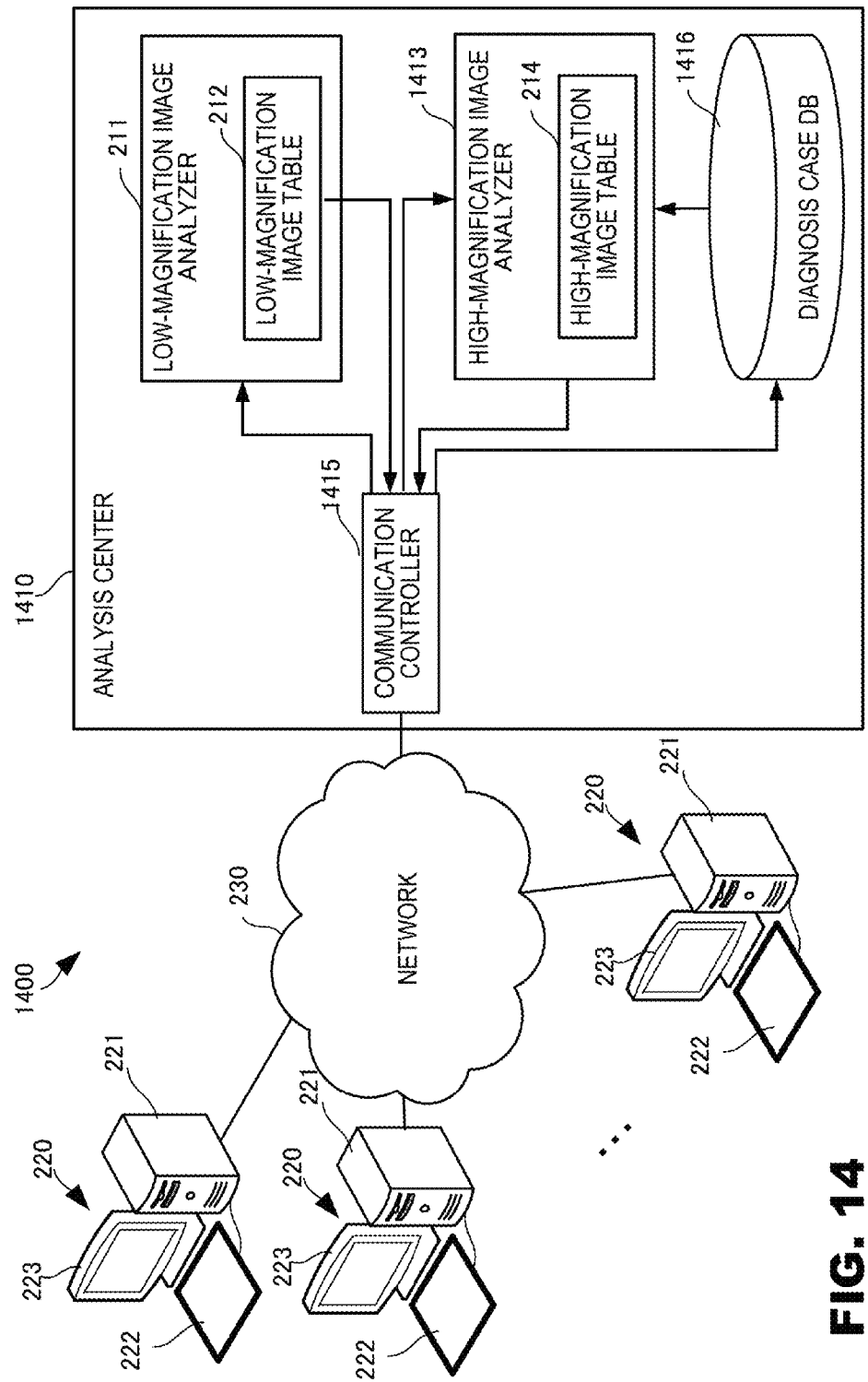
FIG. 14 is a block diagram showing the arrangement of an information processing system including an information processing apparatus according to the fourth embodiment of the present invention.

FIG. 14 is a chart showing the arrangement of a pathological image diagnosis assistance system 1400 serving as an information processing system according to the embodiment. Note that the same reference numerals denote building components having the same functions as those in FIG. 2. A difference of FIG. 14 from FIG. 2 is only the arrangement of an analysis center 1410, and the same reference numerals denote the same functional components.

The pathological image diagnosis assistance system 1400 includes an information processing apparatus functioning as the analysis center 1410, information processing apparatuses functioning as a plurality of pathologist terminals 220, and a network 230 which connects the analysis center 1410 and the pathologist terminals 220.

The analysis center 1410 includes a communication controller 1415 for communicating with the plurality of pathologist terminals 220 via the network 230. The analysis center 1410 also includes a low-magnification image analyzer 211 which analyzes a low-magnification area image of one ROI transmitted from the pathologist terminal 220, and if necessary as a result of the analysis, requests transmission of a high-magnification area image of the same ROI. The low-magnification image analyzer 211 includes a low-magnification image table 212 used for analysis of a low-magnification area image and a high-magnification area image transmission request. Further, the analysis center 1410 includes a high-magnification image analyzer 1413. The high-magnification image analyzer 1413 analyzes a high-magnification area image of the same ROI transmitted from the pathologist terminal 220, and sends back the analysis result as diagnosis assistance information to the pathologist terminal 220. Together with the analysis result, the high-magnification image analyzer 1413 sends back, to the pathologist terminal 220, auxiliary diagnosis information obtained by referring to past area images, analysis results, and diagnosis results accumulated in a diagnosis case DB 1416. The high-magnification image analyzer 1413 includes a high-magnification image table 214 used for analysis of a high-magnification area image and transmission of diagnosis assistance information. The diagnosis case DB 1416 accumulates the tissue sample images, analysis results, and diagnosis results of ROIs in association with each other based on the notifications of diagnosis results obtained by referring to analysis results from the respective pathologist terminals 220. The diagnosis case DB 1416 is looked up to generate auxiliary diagnosis information.

Note that the arrangement of the pathologist terminal 220 is the same as that in the second embodiment, and a description thereof will not be repeated.

<<Operation Sequence of Information Processing System>>

Figure 15:
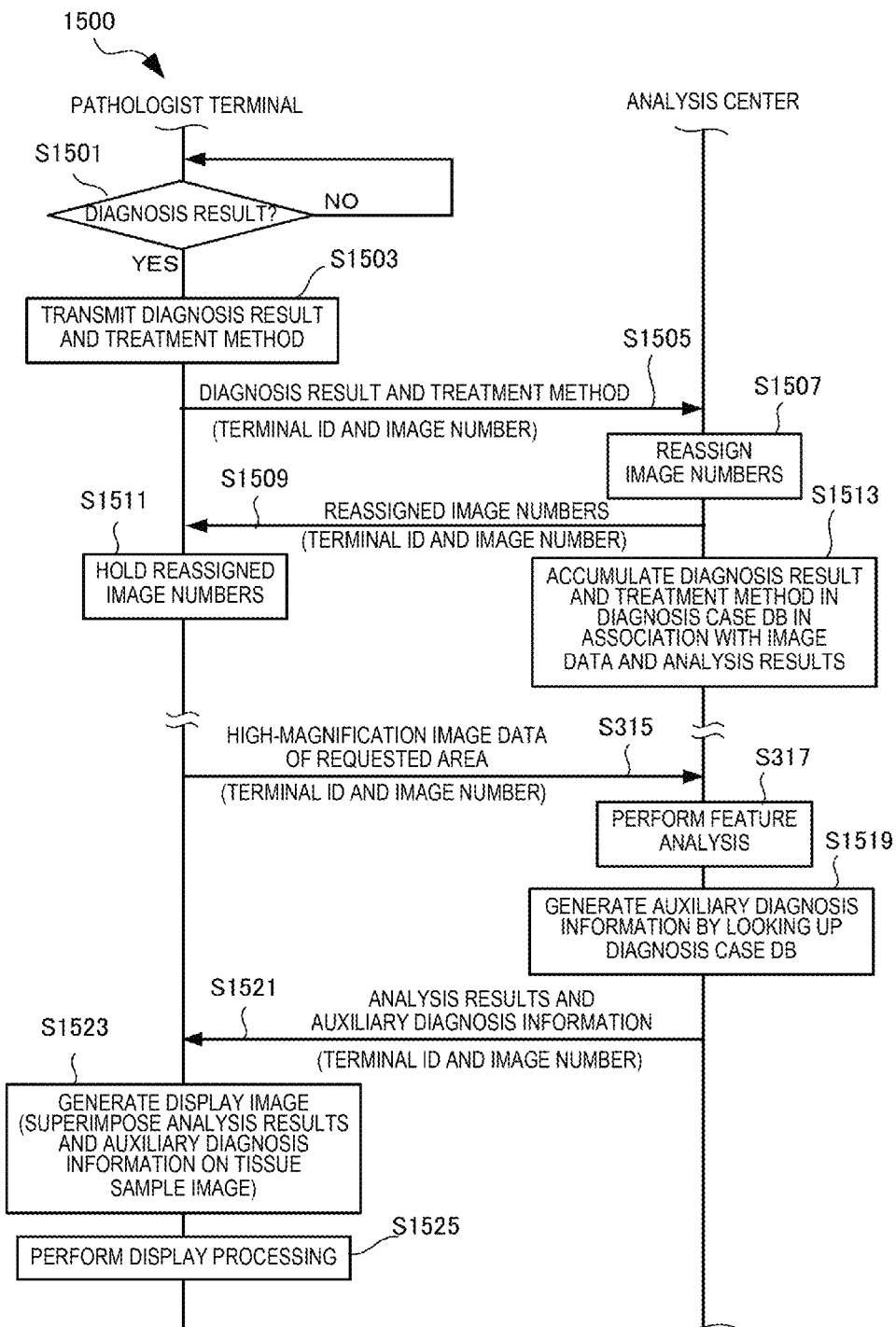
FIG. 15 is a sequence chart showing the operation sequence of the information processing system including the information processing apparatus according to the fourth embodiment of the present invention.

FIG. 15 is a sequence chart showing an operation sequence 1500 of the pathological image diagnosis assistance system 1400 serving as the information processing system according to the embodiment. In FIG. 15, the sequence in FIG. 3 (or FIG. 13) is executed before the start or at an omitted part at the center. However, FIG. 15 does not show this, and shows only a characteristic part of the embodiment. That is, FIG. 15 shows an operation from input of a diagnosis result by a pathologist in the pathologist terminal 220 to accumulation of a case in the diagnosis case DB 1416. The omitted part at the center is accompanied by the operation in FIG. 3 from transmission of requested high-magnification image data of an ROI(s) to display of an analysis result(s) and diagnosis assistance information in the pathologist terminal 220.

After display of analysis results (step S323) in FIG. 3 or 13, in step S1501, the pathologist terminal 220 waits for input of a diagnosis result made by a pathologist by referring to the analysis results. If the diagnosis result is input, the process advances to step S1503, and the pathologist terminal 220 transmits the input diagnosis result and a corresponding treatment method to the analysis center 1410 (see FIG. 16). The pathologist terminal 220 transmits the diagnosis result and treatment method together with a terminal ID, and image numbers for identifying images of the same ROIs as that in FIG. 3 (step S1505).

Upon receiving the diagnosis result and treatment method, in step S1507, the analysis center 1410 reassigns image numbers in the analysis center 1410 in order to accumulate the image of the ROIs in the analysis center 1410 as data independent of the transmission source, patient, and the like. In step S1509, the analysis center 1410 notifies the pathologist terminal 220 of the reassigned image numbers. In step S1511, the pathologist terminal 220 holds the notified reassigned image numbers in association with personal information such as the patient. With this setting, the analysis center 1410 can accumulate and manage data independently of personal information, and if necessary, the pathologist terminal 220 can read out image data of ROIs, analysis of which has been requested by the pathologist terminal 220. In step S1513, the analysis center 1410 accumulates the received diagnosis results and treatment method in the diagnosis case DB 1416 in association with the reassigned image numbers, image data, and analysis results. Note that all pieces of information need not be accumulated in the diagnosis case DB 1416, and information which will help future auxiliary diagnosis may be screened and accumulated. However, when the analysis center 1410 is also used as an information accumulation server for the pathologist terminal 220, all pieces of information transmitted from the pathologist terminal 220 for diagnosis assistance are accumulated.

At the omitted part, the processes in steps S301 to S313 of FIG. 3 are performed in response to a new diagnosis assistance request from the pathologist terminal 220. High-magnification image data is transmitted to the analysis center 1410 in step S315, feature analysis is performed in step S317, and then auxiliary diagnosis information is generated by looking up the diagnosis case DB 1416 in step S1519. In step S1521, the auxiliary diagnosis information is reported to the pathologist terminal 220 together with the diagnosis result. In step S1523, the pathologist terminal 220 generates a display image by superimposing the received diagnosis result and auxiliary diagnosis information on a tissue area selected from a tissue sample image. In step S1525, the display image is displayed on a display 223 to assist diagnosis by the pathologist (see FIG. 17).

<<Display Screen in Pathologist Terminal>>

A display screen on the display 223 in processing according to the embodiment will be explained with reference to FIGS. 16 and 17.

(Display Screen in Diagnosis Result Transmission)

Figure 16:
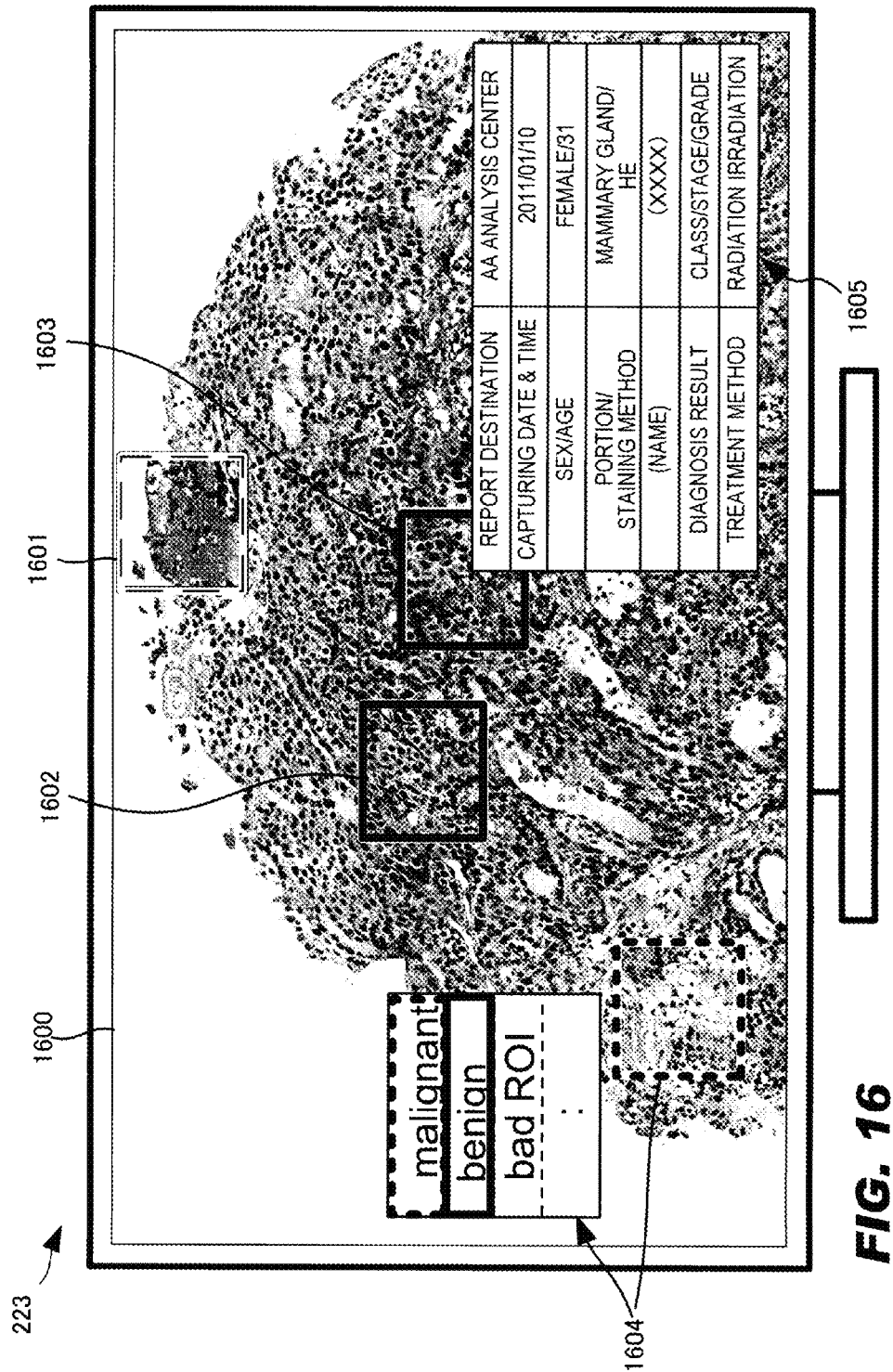
FIG. 16 is a view showing a display screen when transmitting a diagnosis result from a pathologist terminal according to the fourth embodiment of the present invention.

FIG. 16 is a view showing a screen 1600 displayed on the display 223 of the pathologist terminal 220 when transmitting a diagnosis result and treatment method for a selected ROI to the analysis center 1410.

The screen 1600 displays a plurality of selected ROIs 1601 to 1604 which are superimposed on a tissue area selected from a tissue sample image. Of the ROIs 1601 to 1604, the ROI 1601 is deleted from the ROIs by a pathologist. The ROI 1604 is changed from "malignant" to "benign" by the pathologist. The ROIs 1602 and 1603 remain unchanged from analysis results.

In FIG. 16, information 1605 includes management information of the displayed tissue sample image in the pathologist terminal 220, information for identifying the analysis center 1410 as a report destination to which a diagnosis result is reported, and a diagnosis result and treatment method by the pathologist. Of these pieces of information, personal information such as the name is not transmitted to the analysis center 1410. Note that the information 1605 is merely an example, and is not limited to this.

(Display Screen of Analysis Result and Auxiliary Diagnosis Information)

Figure 17:
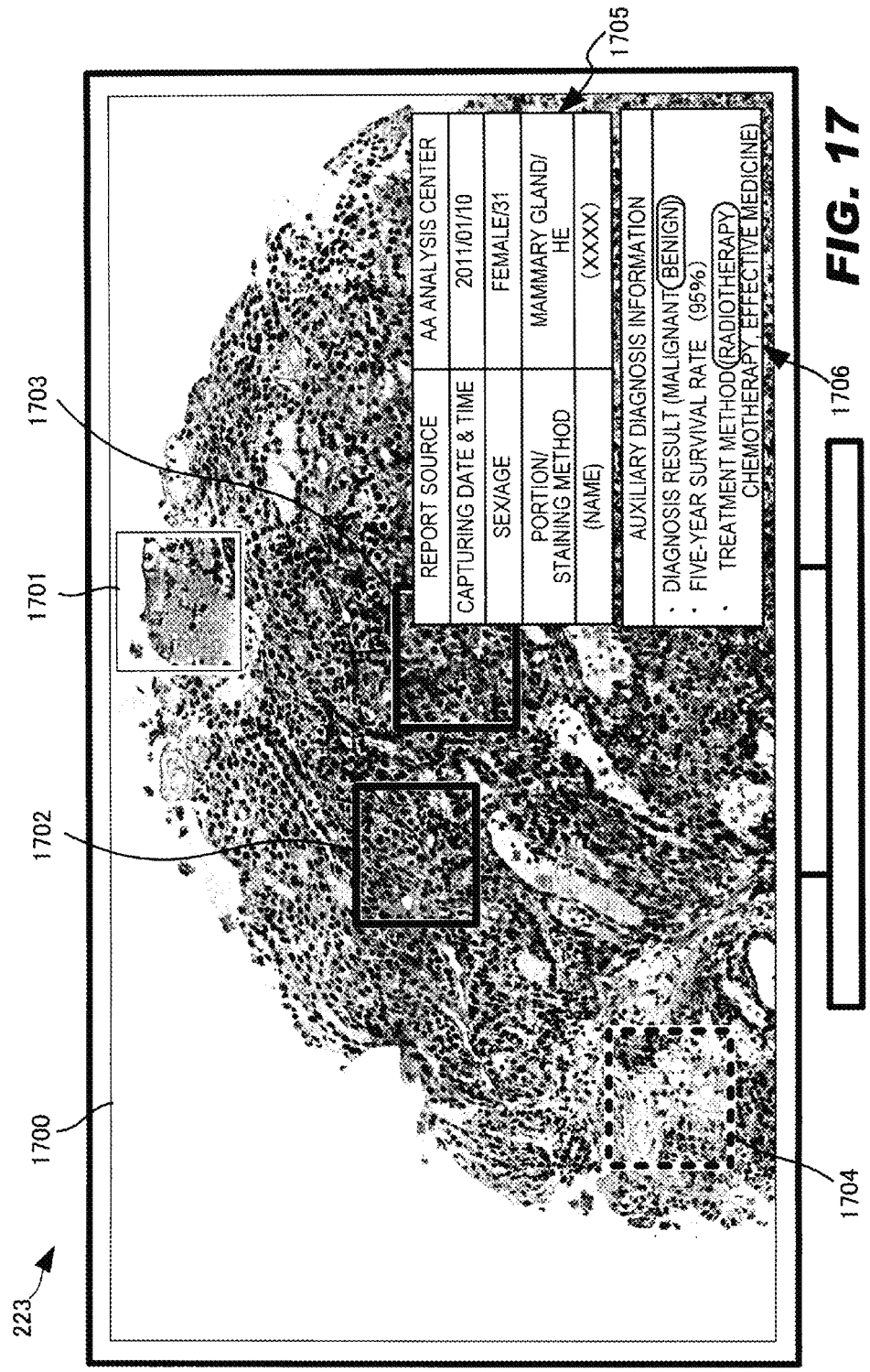
FIG. 17 is a view showing an analysis result display screen on the pathologist terminal according to the fourth embodiment of the present invention.

FIG. 17 is a view showing a screen 1700 obtained by displaying, on the display 223 of the pathologist terminal 220, the result of analysis in the analysis center 1410 and auxiliary diagnosis information.

In FIG. 17, the analysis results of a plurality of ROIs 1701 to 1704 are represented by the difference of the line of a rectangular frame surrounding each ROI. A thin solid line indicates that the ROI 1701 is a cancer cell-free area for which no high-magnification image data need be analyzed. Thick solid lines indicate that the ROIs 1702 and 1703 require analysis of high-magnification image data and are areas where cancer cells are obvious. A thick broken line indicates that the ROI 1704 requires analysis of high-magnification image data but is a cancer cell-free area. Note that the analysis results are represented by the difference of the line of a rectangular frame in FIG. 17, but another identifiable display such as the difference of the color is usable.

In FIG. 17, information 1705 includes management information of the displayed tissue sample image in the pathologist terminal 220, and information for identifying the analysis center 1410 as a report source which has reported the analysis results for diagnosis assistance. Of these pieces of information, personal information such as the name is managed in the pathologist terminal 220. In addition, in FIG. 17, auxiliary diagnosis information 1706 including at least one of information representing whether the condition of a disease is malignant or benign, prediction of a future medical record, and auxiliary information of a treatment plan is displayed. The auxiliary diagnosis information 1706 is generated by looking up the diagnosis case DB 1416 based on the analysis results of image data of ROIs in the analysis center 1410. Note that the pieces of information 1705 and 1706 are merely examples, and are not limited to them. For example, as the auxiliary diagnosis information 1706, information representing whether the symptom is malignant or benign, the average survival time, and the treatment plan are displayed. However, the auxiliary diagnosis information 1706 may include the presence/absence of metastasis, the recurrence rate, and the like.

<<Hardware Arrangement of Analysis Center>>

Figure 18:
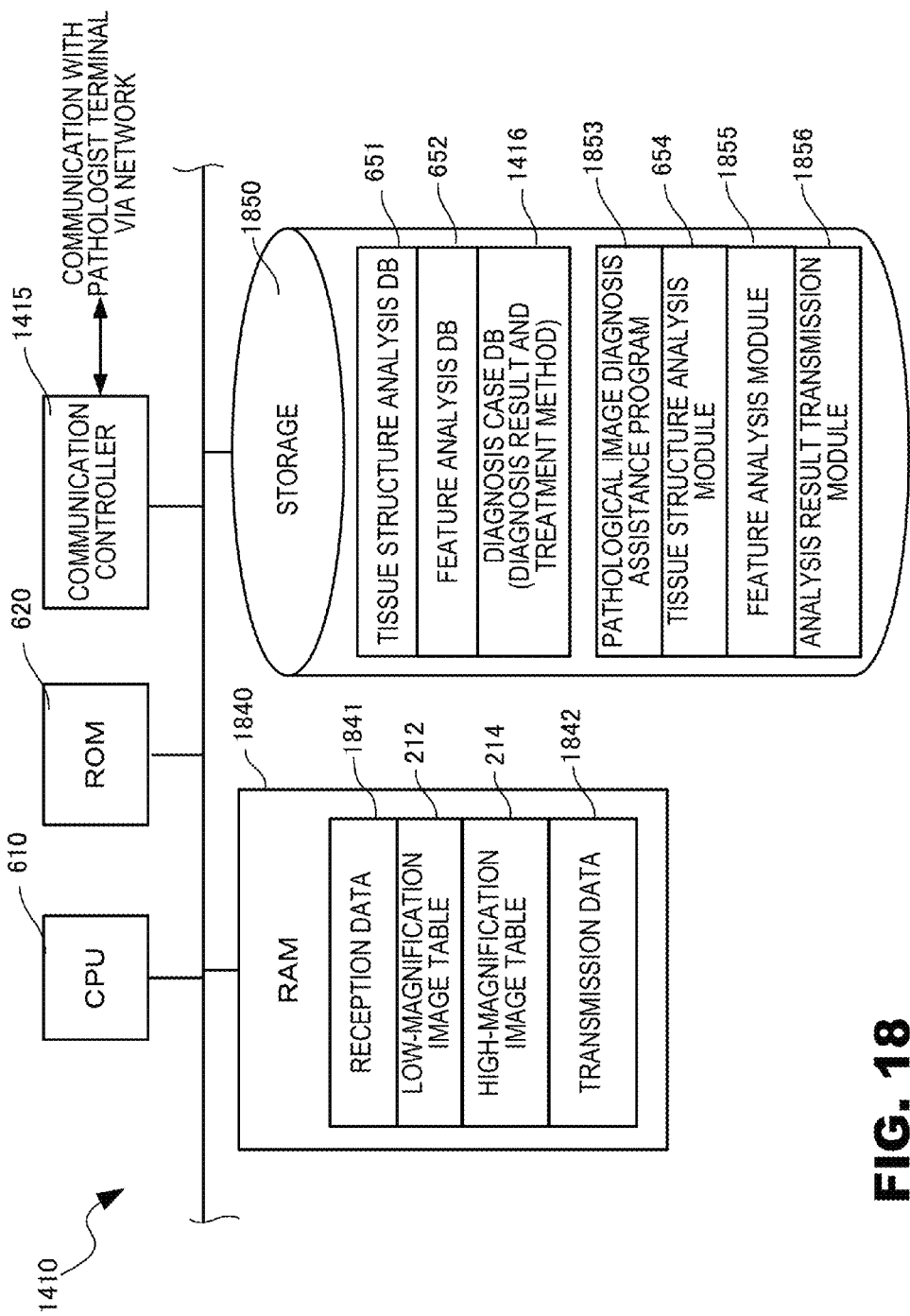
FIG. 18 is a block diagram showing the hardware arrangement of the information processing apparatus according to the fourth embodiment of the present invention.

FIG. 18 is a chart showing the hardware arrangement of the analysis center 1410 according to the embodiment. FIG. 18 shows the arrangement of the analysis center 1410 formed from one apparatus, but the analysis center 1410 may be formed from a plurality of apparatuses for respective functions. In FIG. 18, the same reference numerals as those in FIG. 6 denote the same functional components.

In FIG. 18, a CPU 610 is an arithmetic control processor, and implements the controller of the analysis center 1410 by executing a program. A ROM 620 stores permanent data and programs such as initial data and programs. The communication controller 1415 controls communication with the plurality of pathologist terminals 220 via the network 230. The communication controller 1415 receives a diagnosis result and treatment method from the pathologist terminal 220, and transfers them to the diagnosis case DB 1416. This communication is arbitrarily wired or wireless.

A RAM 1840 is a random access memory used as a temporary storage area by the CPU 610. In the RAM 1840, areas for storing data necessary to implement the embodiment are ensured. Each area stores reception data 1841 including image data of an area image received from the pathologist terminal 220. The reception data 1841 includes a diagnosis result and treatment method in addition to image data of an ROI. The RAM 1840 stores the low-magnification image table 212 for managing low-magnification image data received from the pathologist terminal 220 (see FIG. 7A). Also, the RAM 1840 stores the high-magnification image table 214 for managing high-magnification image data received from the pathologist terminal 220 (see FIG. 7B). Further, the RAM 1840 stores transmission data 1842 which is to be transmitted to the pathologist terminal 220, and includes analysis results. In addition to the analysis results, the transmission data 1842 includes auxiliary diagnosis information.

A storage 1850 is a large-capacity storage device which stores databases, various parameters, and programs to be executed by the CPU 610 in a nonvolatile way. The storage 1850 stores the following data or programs necessary to implement the embodiment. As a data storage, the storage 1850 stores a tissue structure analysis DB 651 used to perform tissue structure analysis of an ROI based on low-magnification image data. Also, the storage 1850 stores a feature analysis DB 652 used to perform feature analysis of an ROI based on high-magnification image data. Further, the storage 1850 stores the diagnosis case DB 1416 which accumulates diagnosis results and treatment methods in association with image data of ROIs (see FIG. 19).

Figure 20:
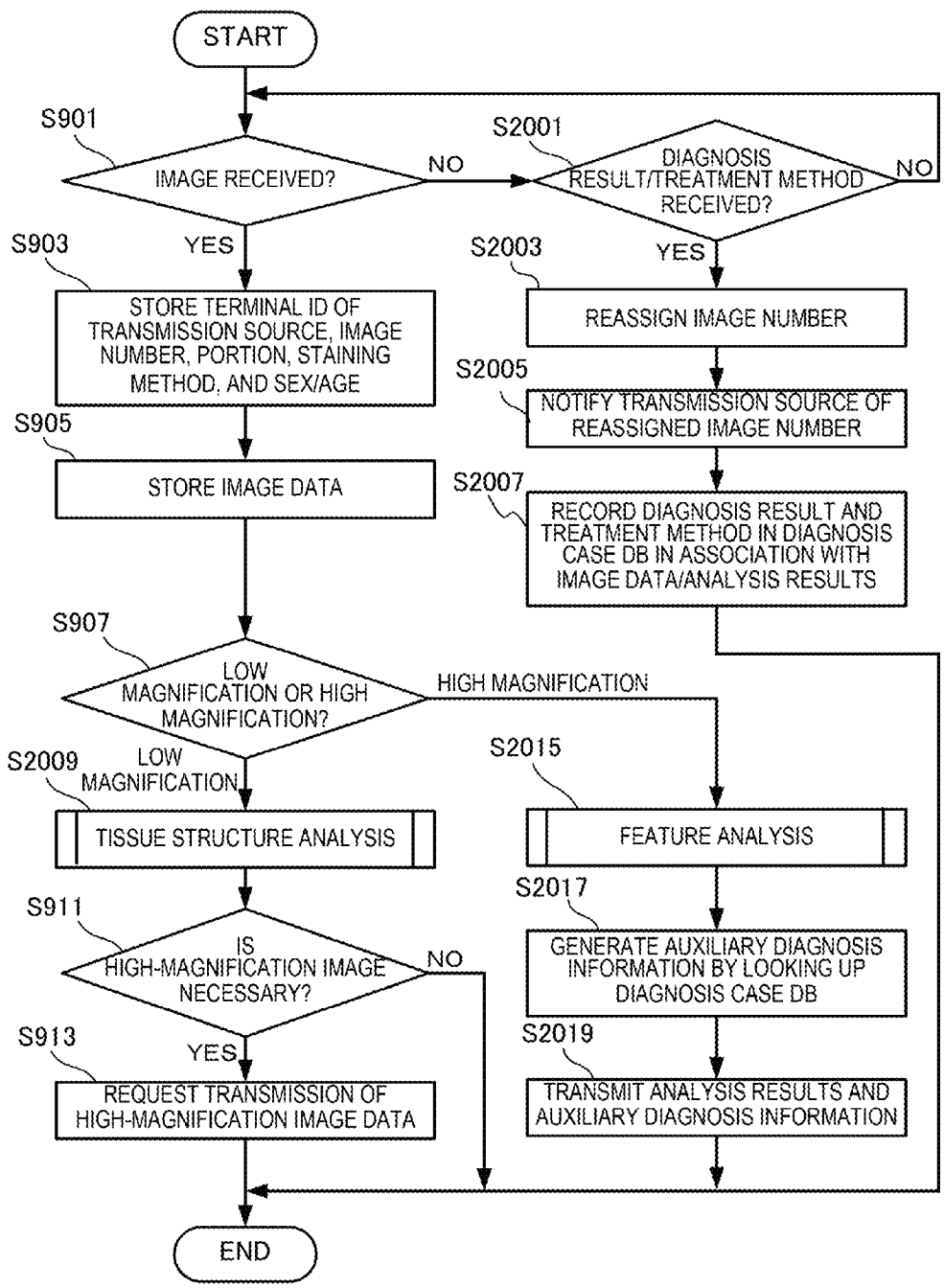
FIG. 20 is a flowchart showing the processing procedure of the information processing apparatus according to the fourth embodiment of the present invention.

In the embodiment, as a program, the storage 1850 stores a pathological image diagnosis assistance program 1853 which implements a series of pathological image diagnosis assistances (see FIG. 20). The storage 1850 stores a tissue structure analysis module 654 which forms part of the pathological image diagnosis assistance program 1853, and performs tissue structure analysis of an ROI based on low-magnification image data by using the tissue structure analysis DB 651. The storage 1850 stores a feature analysis module 1855 which forms part of the pathological image diagnosis assistance program 1853, performs feature analysis of an ROI based on high-magnification image data by using the feature analysis DB 652, and generates auxiliary diagnosis information by looking up the diagnosis case DB 1416. The storage 1850 stores an analysis result transmission module 1856 which transmits analysis results and auxiliary diagnosis information as diagnosis assistance information to the pathologist terminal 220.

FIG. 18 shows only data and programs necessary for the embodiment, and does not show general-purpose data and programs such as an OS.

(Diagnosis Case DB)

FIG. 19 is a chart showing the structure of data accumulated in the diagnosis case DB 1416. The diagnosis case DB 1416 manages data by image numbers reassigned uniquely by the analysis center 1410. The data are completely independent of personal information such as the patient and transmission source, and managed for respective ROIs. Only the pathologist terminal 220 serving as a transmission source is notified of the reassigned image number. Therefore, personal information does not leak outside, and the transmission source can always access the data.

The diagnosis case DB 1416 is managed by a reassigned image number 1901. High-magnification image data 1902 of an ROI is stored in correspondence with each reassigned image number 1901. In the high-magnification image data 1902, a pointer pointing a storage address of image data stored at another position may be stored. Also, the diagnosis case DB 1416 stores link information 1903 and accumulation date & time 1904 of an image to represent the transition of a symptom of the same patient. Further, the diagnosis case DB 1416 stores a portion 1905 of a tissue, a staining method 1906, and a sex/age 1907 associated with an analysis method and diagnosis method. The diagnosis case DB 1416 stores an analysis result 1908 of image data in the analysis center 1410, and a diagnosis result 1909 and treatment method 1910 determined by a pathologist at the transmission source using the analysis results 1908 as assistance information.

<<Operation Procedure of Analysis Center>>

FIG. 20 is a flowchart showing the operation procedure of the analysis center 1410. The CPU 610 in FIG. 18 executes this flowchart by using the RAM 640, thereby implementing the function of the analysis center 1410 in FIG. 14. Note that the same reference numerals as those in FIG. 9 denote the same steps.

First, in step S901, the analysis center 1410 waits for reception of an image from the pathologist terminal 220. If the analysis center 1410 receives an image, the process advances to step S903, and the analysis center 1410 stores and holds information including the terminal ID of the transmission source of the received image data, the image number, the portion, the staining method, and the sex/age. In step S905, the analysis center 1410 stores and holds the transmitted image data. In the embodiment, which of low-magnification image data and high-magnification image data is the received image data is discriminated from the image number, and the pieces of information stored and held in steps S903 and S905 are stored in the low-magnification image table 212 of FIG. 7A or the high-magnification image table 214 of FIG. 7B.

If no image is received (NO in step S901), the analysis center 1410 judges in step S2001 whether the diagnosis result and treatment method are received. If the diagnosis result and treatment method are received, the process advances to step S2003, and the analysis center 1410 uniquely reassigns an image number. In step S2005, the analysis center 1410 notifies only the pathologist terminal 220 serving as the transmission source of the reassigned image number. In step S2007, the analysis center 1410 adds the diagnosis result and treatment method to the image data and analysis results of ROIs, and records them in the diagnosis case DB 1416.

In step S907, the process branches in correspondence with the discrimination of which of low-magnification image data and high-magnification image data is the received image data. If the received image data is low-magnification image data, the process advances to step S2009, and the analysis center 1410 performs tissue structure analysis of the low-magnification image data corresponding to the portion, staining method, sex/age, and the like. Note that the tissue structure analysis performed in step S2009 can use information in the diagnosis case DB 1416, which will not be described in detail. Then, in step S911, the analysis center 1410 judges, from the result of the tissue structure analysis, whether analysis of a high-magnification image of the same ROI is necessary. If analysis of a high-magnification image of the same ROI is necessary, the process advances to step 913, and the analysis center 1410 requests the pathologist terminal 220 serving as the transmission source to transmit high-magnification image data of the same ROI.

If the received image data is high-magnification image data, the process advances to step S2015, and the analysis center 1410 performs feature analysis of the high-magnification image data corresponding to the portion, staining method, sex/age, and the like. In the embodiment, the analysis center 1410 generates auxiliary diagnosis information by looking up the diagnosis case DB 1416 in step S2017. In step S2019, the analysis center 1410 transmits the feature analysis result of the high-magnification image data and the auxiliary diagnosis information to the pathologist terminal 220 serving as the transmission source together with the image number obtained from the transmission source.

<<Hardware Arrangement of Pathologist Terminal>>

The hardware arrangement of the pathologist terminal is basically the same as that in FIG. 10, and a description thereof will not be repeated.

(Patient History DB)

Figure 21:
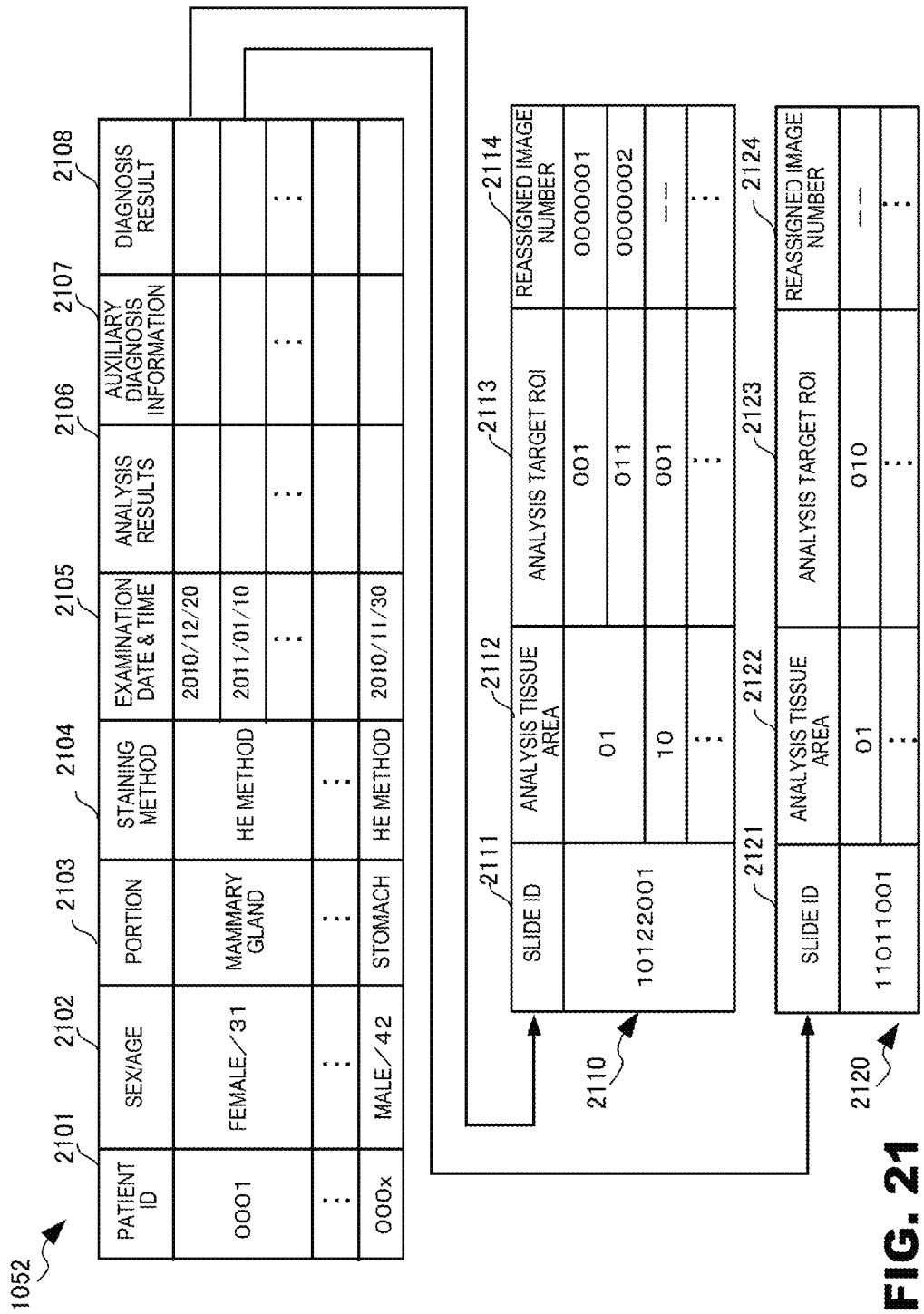
FIG. 21 is a chart showing the structure of a patient history DB according to the fourth embodiment of the present invention.

FIG. 21 is a chart showing the structure of a patient history DB 1052 shown in FIG. 10.

In the upper view of FIG. 21, reference numeral 2101 denotes a patient ID for identifying a patient; and 2102, a sex/age of a patient that is information for specifying a patient. Although another specifying information such as the address of a patient is also stored, FIG. 21 shows only information necessary for processing in the embodiment. Reference numeral 2103 denotes a portion of a tissue sample image to be analyzed; and 2104, a staining method for the tissue that is information associated with an analysis method in the analysis center 1410. Reference numeral 2105 denotes an examination date & time when a target tissue sample image was obtained.

The patient history DB 1052 stores, for each examination, analysis results 2106 from the analysis center 1410, auxiliary diagnosis information 2107 from the analysis center 1410, and a diagnosis result 2108 by a pathologist, which are pieces of information as the examination result.

The lower view of FIG. 21 shows information for specifying image data. Reference numeral 2111 denotes a slide ID for identifying a pathological slide; 2112, an analysis tissue area representing a tissue area to be analyzed in a tissue sample image read from a pathological slide by a scanner 222; and 2113, an analysis target ROI representing an ROI to be analyzed in a tissue area. In the embodiment, a reassigned image number 2114 is registered for image data accumulated in the diagnosis case DB 1416 of the analysis center 1410. Hence, image data having no reassigned image number 2114 is not accumulated in the diagnosis case DB 1416 of the analysis center 1410. In this way, the presence/absence of the reassigned image number 2114 serves as a barometer of whether the image was used for diagnosis. Information for specifying image data is registered in correspondence with each examination, like 2110 and 2120.

<<Operation Procedure of Pathologist Terminal>>

Figure 22:
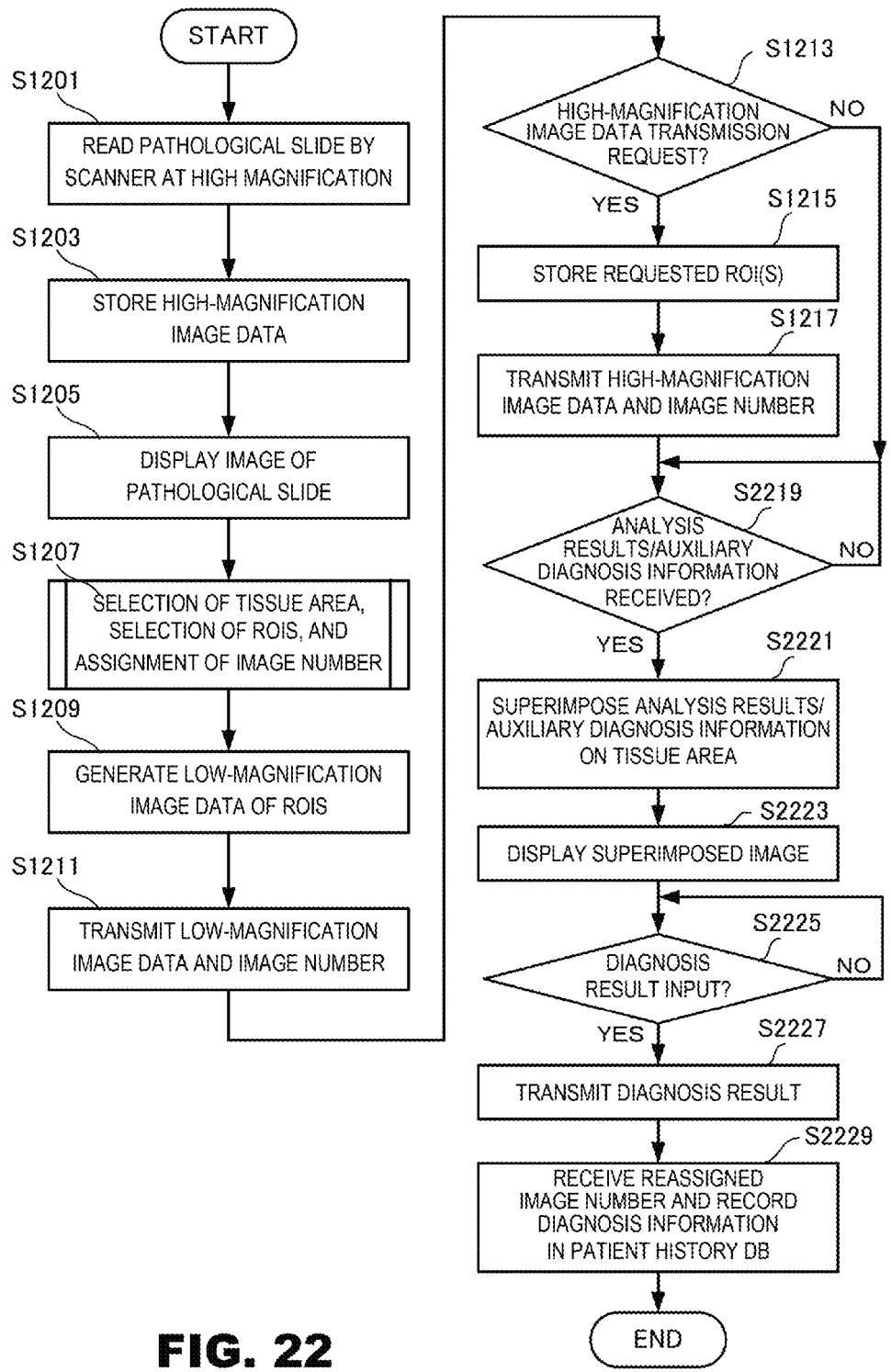
FIG. 22 is a flowchart showing the processing procedure of the pathologist terminal according to the fourth embodiment of the present invention.

FIG. 22 is a flowchart showing the operation procedure of the pathologist terminal 220 according to the embodiment. A CPU 1010 in FIG. 10 executes this flowchart by using a RAM 1040, thereby implementing the function of the pathologist terminal 220 in FIG. 14. Note that steps S1201 to S1217 in FIG. 22 are the same as those in FIG. 12, and a description thereof will not be repeated.

In step S2219, the pathologist terminal 220 waits for reception of analysis results and auxiliary diagnosis information. If the pathologist terminal 220 receives analysis results and auxiliary diagnosis information, the process advances to step S2221, and the pathologist terminal 220 generates a display screen by superimposing the analysis results and auxiliary diagnosis information on a tissue area. In step S2223, the pathologist terminal 220 displays the superimposed image (see FIG. 17).

In step S2225, the pathologist terminal 220 waits for input of a diagnosis result by a pathologist. If the diagnosis result by the pathologist is input, the process advances to step S2227, and the pathologist terminal 220 transmits the diagnosis result to the analysis center 1410. In step S2229, the pathologist terminal 220 receives reassigned image numbers from the analysis center 1410, and records them in the patient history DB 1052 of FIG. 21. Holding information associated with diagnosis in the analysis center 1410 together with image data reduces the amount of data accumulated in the pathologist terminal 220 (see FIG. 21).

Fifth Embodiment

In the second to fifth embodiments, image data of an ROI is transmitted from the pathologist terminal 220 to the analysis center 210 or 1410 without the mediacy of diagnosis by a pathologist. The fifth embodiment will explain processing of requesting diagnosis assistance of an analysis center 210 for a tissue sample image for which diagnosis by a pathologist is difficult regardless of local or remote diagnosis. According to the fifth embodiment, diagnosis assistance is requested not for all tissue sample images, but only when diagnosis by a pathologist is difficult. While reducing the burden on the analysis center 210, assistance of the analysis center for diagnosis by a pathologist based on a tissue sample image can be quickly received at high accuracy.

The arrangements of an information processing system, analysis center, and a pathologist terminal according to the fifth embodiment are similar to those in the fourth embodiment and can be inferred, so a description thereof will not be repeated.

<<Operation Sequence of Information Processing System>>

FIG. 23 is a sequence chart showing an operation sequence 2300 of a pathological image diagnosis assistance system 1400 serving as the information processing system according to the embodiment.

First, a scanner 222 reads a pathological slide in step S2301, and diagnosis processing by a pathologist is performed locally or remotely in step S2303. In step S2305, it is judged whether the diagnosis is difficult. If the diagnosis is easy, the patient is notified of the diagnosis result.

If the diagnosis is difficult, the process advances to step S2307 to select an ROI of a tissue area, analysis of which is requested for diagnosis assistance. This ROI selection is selection of a location where judgment is difficult in diagnosis. In step S2309, high-magnification image data of the selected ROI is transmitted to the analysis center 210 to request analysis.

Processes from analysis processing (step S1517) in the analysis center 210 to display (step S1525) on a display 223 of a pathologist terminal 220 are the same as those in FIG. 15, and a description thereof will not be repeated. Even when the analysis center 210 is requested to analyze a location where judgment is difficult, processing of the embodiment to transmit low-magnification image data first, and if necessary, transmit high-magnification image data may be applied.

Other Embodiments

The above embodiments have mainly explained a case in which a cancer is detected from a tissue sample image using the HE method as the staining method. However, the present invention is further applicable to a case in which whether a cancer region is positive or negative is determined from a tissue sample image immunostained by the IHC method. For example, the IHC method for a mammary duct uses, as features, the ratio of nuclei stained in brown, the ratio of unstained nuclei (blue nuclei), and the entire concentric staining of a membrane (whether the entire membrane is stained). In the IHC method, whether ER/PR or Her2 is positive or negative is judged at a fixed magnification (for example, 20×) for a region known to have a cancer. In accordance with this result, a treatment method is selected. When a tissue sample image is remotely analyzed by the IHC method, it is also conceivable to transmit, to an analysis center 210, a 20× image of a tissue sample image which is formed from serial sections for a cancer region detected from a tissue sample image obtained by the HE method, and receive a negative/positive result.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The present invention can be applied to a system including plural devices or a single apparatus. The present invention can be applied to a case in which a control program for implementing the functions of the embodiments is supplied to the system or apparatus directly or from a remote site. Hence, the control program installed in a computer to implement the functions of the present invention by the computer, a medium storing the control program, or a WWW (World Wide Web) server to download the control program is also incorporated in the present invention.

This application claims the benefit of Japanese Patent Application No. 2011-012425 filed on Jan. 24, 2011, which is hereby incorporated by reference herein in its entirety.

The invention claimed is:

1. An information processing apparatus which assists with a diagnosis based on a tissue sample image obtained by staining and capturing a tissue, the information processing apparatus comprising:

a processor, a memory, and a communication controller, wherein:

the communication controller comprises: a first receiver that receives, from an information apparatus requesting assistance with the diagnosis, lower-magnification image data among a plurality of image data obtained at different magnifications for an area image selected within the tissue sample image;

the processor comprises: a first analyzer that analyzes the area image based on the lower-magnification image data received by said first receiver, and generates first feature information;

the processor further comprises: a determination unit that determines whether analysis based on higher-magnification image data is necessary for the area image, based on the first feature information generated by said first analyzer;

the communication controller further comprises: a notification unit that transmits, to the information apparatus requesting assistance with the diagnosis, a request for transmitting the higher-magnification image data for the area image, when said determination unit determines that analysis based on the higher-magnification image data is necessary;

the communication controller further comprises: a second receiver that receives, from the information apparatus requesting the assistance with the diagnosis, the higher-magnification image data transmitted in response to the transmission request from said notification unit;

the processor further comprises: a second analyzer that analyzes the area image based on the higher-magnification image data received by said second receiver, and generates second feature information; and the communication controller further comprises: a transmitter that transmits, to the information apparatus requesting the assistance with the diagnosis, the second feature information generated by said second analyzer.

2. The information processing apparatus according to claim 1, wherein the processor further comprises a management unit that manages image data of the area image in association with transmission source identifying information for identifying a transmission source of the image data, and image data identifying information for identifying the image data, wherein said first receiver and said second receiver receive the image data of the area image together with the transmission source identifying information and the image data identifying information, said notification unit notifies the request of transmitting the higher magnification image data, together with the transmission source identifying information and the image data identifying information, and said transmitter transmits the second feature information generated by said second analyzer together with the transmission source identifying information and the image data identifying information.

3. The information processing apparatus according to claim 2, wherein the image data identifying information comprises information for specifying a portion of an organism of the tissue sample image, and
analysis by said first analyzer and said second analyzer and determination by said determination unit are analysis and determination corresponding to the portion of the organism of the tissue sample image, respectively.

4. The information processing apparatus according to claim 2, wherein the image data identifying information comprises information for specifying a staining method of the tissue sample image, and
analysis by said first analyzer and said second analyzer and determination by said determination unit are analysis and determination corresponding to the staining method of the tissue sample image, respectively.

5. The information processing apparatus according to claim 4, wherein the staining method comprises an HE method.

6. The information processing apparatus according to claim 1, wherein the first feature information generated by said first analyzer comprises a stained tissue structure in the area image.

7. The information processing apparatus according to claim 6, wherein the tissue structure comprises a duct shape.

8. The information processing apparatus according to claim 6, wherein said determination unit determines that analysis based on the higher magnification image data is necessary for the area image, when the stained tissue structure in the area image is judged to be a cancer cell candidate.

9. The information processing apparatus according to claim 1, wherein the second feature information generated by said second analyzer comprises a feature regarding a stained cell in the area image.

10. The information processing apparatus according to claim 9, wherein the feature comprises an average nucleus size, an average nuclear grade, and a texture.

11. The information processing apparatus according to claim 1,
wherein the communication controller further comprises:
a third receiver that receives, from the information apparatus requesting assistance with the diagnosis, a diagnosis result associated with image data of the area image; and
wherein the processor further comprises:
an accumulator that accumulates, as a diagnosis case, the image data of the area image in association with the diagnosis result received by said third receiver; and
a generator that generates auxiliary diagnosis information from the image data of the area image received by said second receiver by referring to image data accumulated in said accumulator,
wherein said transmitter further transmits the auxiliary diagnosis information generated by said generator.

12. The information processing apparatus according to claim 11, wherein the auxiliary diagnosis information generated by said generator comprises at least one of information representing whether a condition of a disease is malignant or benign, an average survival time, presence/absence of metastasis, a recurrence rate, and auxiliary information of a treatment plan.

13. A method for controlling an information processing apparatus which assists diagnosis based on a tissue sample image obtained by staining and capturing a tissue, comprising:
receiving lower magnification image data among a plurality of image data obtained at different magnifications for an area image selected in the tissue sample image;
analyzing the area image based on the received lower magnification image data, and generating first feature information;
determining whether analysis based on higher magnification image data is necessary for the area image, based on the generated first feature information;
notifying a transmission request for transmitting the higher magnification image data for the area image, when analysis based on the higher magnification image data is determined to be necessary;
receiving the higher magnification image data transmitted in response to the transmission request;
analyzing the area image based on the received higher magnification image data, and generating second feature information; and
transmitting the generated second feature information.

14. A non-transitory computer-readable storage medium storing a program for controlling an information processing apparatus which assists diagnosis based on a tissue sample image obtained by staining and capturing a tissue, the control program causing a computer to execute:
receiving lower magnification image data among a plurality of image data obtained at different magnifications for an area image selected in the tissue sample image;
analyzing the area image based on the received lower magnification image data, and generating first feature information;
determining whether analysis based on higher magnification image data is necessary for the area image, based on the generated first feature information;
notifying a transmission request for transmitting the higher magnification image data for the area image, when analysis based on the higher magnification image data is determined to be necessary;
receiving the higher magnification image data transmitted in response to the transmission request;
analyzing the area image based on the received higher magnification image data, and generating second feature information; and
transmitting the generated second feature information.

* * * * *